US009121055B2

(12) United States Patent
Ludowise

(10) Patent No.: US 9,121,055 B2
(45) Date of Patent: Sep. 1, 2015

(54) ANALYSIS OF NUCLEIC ACID AMPLIFICATION CURVES USING WAVELET TRANSFORMATION

(75) Inventor: Peter D. Ludowise, Cottage Grove, MN (US)

(73) Assignee: 3M INNOVATIVE PROPERTIES COMPANY, St. Paul, MN (US)

( * ) Notice: Subject to any disclaimer, the term of this patent is extended or adjusted under 35 U.S.C. 154(b) by 811 days.

(21) Appl. No.: 12/988,820

(22) PCT Filed: Apr. 24, 2009

(86) PCT No.: PCT/US2009/041656
§ 371 (c)(1),
(2), (4) Date: Oct. 21, 2010

(87) PCT Pub. No.: WO2009/132268
PCT Pub. Date: Oct. 29, 2009

(65) Prior Publication Data
US 2011/0039274 A1    Feb. 17, 2011

Related U.S. Application Data

(60) Provisional application No. 61/047,606, filed on Apr. 24, 2008.

(51) Int. Cl.
*C12Q 1/68* (2006.01)
*G06F 19/00* (2011.01)

(52) U.S. Cl.
CPC .................................. *C12Q 1/6851* (2013.01)

(58) Field of Classification Search
None
See application file for complete search history.

(56) References Cited

U.S. PATENT DOCUMENTS

| | | |
|---|---|---|
| 3,918,793 A | 11/1975 | Kraft |
| 3,949,231 A | 4/1976 | Blunck |
| 4,343,991 A | 8/1982 | Fujiwara |
| 4,726,676 A | 2/1988 | Maslaney |
| 4,909,990 A | 3/1990 | Block |
| 4,927,766 A | 5/1990 | Auerbach |
| 5,296,958 A | 3/1994 | Roddy |
| 5,414,600 A | 5/1995 | Strobl |
| 5,473,437 A | 12/1995 | Blumenfeld |
| 5,585,069 A | 12/1996 | Zanzucchi |
| 5,639,668 A | 6/1997 | Neel |
| 5,741,874 A | 4/1998 | Iizawa |
| 5,751,874 A | 5/1998 | Chudoba |
| 5,766,889 A | 6/1998 | Atwood |
| 5,863,736 A | 1/1999 | Haaland |
| 5,928,907 A | 7/1999 | Woudenber |
| 5,994,150 A | 11/1999 | Challener |
| 6,015,674 A | 1/2000 | Woudenberg |
| 6,144,448 A | 11/2000 | Mitoma |
| 6,161,946 A | 12/2000 | Bishop |
| 6,232,075 B1 | 5/2001 | Williams |
| 6,333,501 B1 | 12/2001 | Labrenz |
| 6,339,473 B1 | 1/2002 | Gordon |
| 6,342,349 B1 | 1/2002 | Virtanen |
| 6,442,116 B2 | 8/2002 | Asano |
| 6,537,211 B1 | 3/2003 | Wang |
| 6,563,113 B1 | 5/2003 | Amann |
| 6,563,581 B1 | 5/2003 | Oldham |
| 6,597,450 B1 | 7/2003 | Andrews |
| 6,597,832 B2 | 7/2003 | Cheng |
| 6,616,304 B2 | 9/2003 | Li |
| 6,627,159 B1 | 9/2003 | Bedingham |
| 6,734,401 B2 | 5/2004 | Bedingham |
| 6,803,999 B1 | 10/2004 | Gordon |
| 6,806,954 B2 | 10/2004 | Sandstrom |
| 6,814,935 B2 | 11/2004 | Harms |
| 6,821,771 B2 | 11/2004 | Festoc |
| 6,833,536 B2 | 12/2004 | Shigeura |
| 6,950,755 B2 * | 9/2005 | Stahl ................................ 702/19 |
| 6,992,278 B2 | 1/2006 | Sjoberg |
| 6,992,769 B2 | 1/2006 | Gordon |
| 7,026,168 B2 | 4/2006 | Bedingham |
| 7,088,650 B1 | 8/2006 | Worthington |
| 7,238,269 B2 | 7/2007 | Gason |
| 7,322,254 B2 | 1/2008 | Bedingham |
| 7,435,602 B2 | 10/2008 | Gunstream |

(Continued)

FOREIGN PATENT DOCUMENTS

| | | |
|---|---|---|
| CN | 1311436 | 9/2001 |
| CN | 2522854 Y | 11/2002 |

(Continued)

OTHER PUBLICATIONS

Moore Jr., (Journal of Neuroscience, 2002, 22(20):8932-8941).*
Demiralp et al. (Cerebral Cortex, 2007, 17:1007-1019).*
Kevin R. Coombes, et al: "Improved Peak Detection and Quantification of Mass Spectrometry Data Acquired From Surface-Enhanced Laser Desorption and Ionization by Denoising Spectra With the Undecimated Discrete Wavelet Transform" Proteomics, vol. 5, No. 16, Nov. 1, 2005, pp. 4107-4117, XP55009873, ISSN 1615-9853.
J.S. Morris, et al, Feature Extraction and Quantification for Mass Spectrometry in Biomedical Applications Using the Mean Spectrum, Bioinformatics, vol. 21, No. 9, Jan. 26, 2005, pp. 1764-1775, XP55009676, ISSN: 1367-4803.
D. A. Adjeroh, "On Denoising and Compression of DNA Microarray Images" Pattern Recognition, Elsevier, GB, vol. 39, No. 12, Dec. 1, 2006, pp. 2478-2493, XP025226747, ISSN 0031-3203.
Bagwell, "Fluorescence Spectral Overlap Compensation for Any Number of Flow Cytometry Parameters", Annals New York Academy of Sciences, Mar. 1993, vol. 677, pp. 167-184.

(Continued)

*Primary Examiner* — Stephanie K Mummert
(74) *Attorney, Agent, or Firm* — X. Christina Huang

(57) ABSTRACT

A method comprising acquiring amplification data proportional to an amount of nucleic acid present for each of a plurality of PCR cycles includes applying wavelet transformation to the amplification data to determine a PCR cycle corresponding to a point within a growth period of the amplification data, and updating a display A device including a control module, an analysis module and an interface module for initialization of PCR analysis of a nucleic acid sample, receiving amplification data proportional to an amount of nucleic acid present applying wavelet transformation to the amplification data to determine a PCR cycle corresponding to a point within a growth period of the amplification data, and updating a display based on the amplification data is also provided.

47 Claims, 20 Drawing Sheets

(56) References Cited

U.S. PATENT DOCUMENTS

| | | | |
|---|---|---|---|
| 7,507,575 B2 | 3/2009 | Bedingham | |
| 7,527,763 B2 | 5/2009 | Bedingham | |
| 7,709,249 B2 | 5/2010 | Bedingham | |
| 7,754,474 B2 | 7/2010 | Aysta | |
| 2001/0029036 A1 | 10/2001 | Landers | |
| 2001/0046712 A1 | 11/2001 | Hang | |
| 2001/0052927 A1 | 12/2001 | Takase | |
| 2002/0028452 A1 | 3/2002 | Wittwer | |
| 2002/0039333 A1 | 4/2002 | Tsukahara | |
| 2002/0043626 A1 | 4/2002 | Booker | |
| 2002/0047003 A1 | 4/2002 | Bedingham | |
| 2002/0048533 A1 | 4/2002 | Harms | |
| 2002/0064885 A1 | 5/2002 | Bedingham | |
| 2002/0076354 A1 | 6/2002 | Cohen | |
| 2002/0104884 A1 | 8/2002 | Meier | |
| 2002/0172980 A1 | 11/2002 | Phan | |
| 2003/0003459 A1 | 1/2003 | Stahl | |
| 2003/0044826 A1 | 3/2003 | Ward | |
| 2003/0054563 A1 | 3/2003 | Ljungstrom | |
| 2003/0077598 A1 | 4/2003 | Phan | |
| 2003/0100998 A2 | 5/2003 | Brunner | |
| 2003/0104394 A1 | 6/2003 | Dai | |
| 2003/0130823 A1* | 7/2003 | Potyrailo et al. | 702/189 |
| 2003/0190184 A1 | 10/2003 | O'Brien | |
| 2003/0219754 A1 | 11/2003 | Oleksy | |
| 2004/0067051 A1 | 4/2004 | Kylberg | |
| 2004/0072335 A1 | 4/2004 | Boege | |
| 2004/0126279 A1 | 7/2004 | Renzi | |
| 2004/0224317 A1 | 11/2004 | Kordunsky | |
| 2005/0012199 A1 | 1/2005 | Rosenau | |
| 2005/0014249 A1 | 1/2005 | Staimer | |
| 2005/0023765 A1 | 2/2005 | Coombs | |
| 2005/0030395 A1 | 2/2005 | Hattori | |
| 2005/0032052 A1 | 2/2005 | Pal | |
| 2005/0048595 A1 | 3/2005 | Yamatsu | |
| 2005/0059062 A1 | 3/2005 | Kaiser | |
| 2005/0064582 A1 | 3/2005 | Wittwer | |
| 2005/0074784 A1 | 4/2005 | Vo-Dinh | |
| 2005/0109396 A1 | 5/2005 | Zucchelli | |
| 2005/0130177 A1 | 6/2005 | Bedingham | |
| 2005/0151972 A1 | 7/2005 | Boege | |
| 2005/0165558 A1 | 7/2005 | Becker | |
| 2006/0223169 A1 | 10/2006 | Bedingham | |
| 2006/0223172 A1 | 10/2006 | Bedingham | |
| 2006/0286587 A1* | 12/2006 | Lee et al. | 435/6 |
| 2007/0001007 A1 | 1/2007 | Koenck | |
| 2007/0009382 A1 | 1/2007 | Bedingham | |
| 2007/0009383 A1 | 1/2007 | Bedingham | |
| 2007/0010007 A1 | 1/2007 | Aysta | |
| 2007/0098594 A1 | 5/2007 | Elkin | |
| 2007/0143385 A1 | 6/2007 | Kurnik | |
| 2008/0018898 A1 | 1/2008 | Gunstream | |
| 2008/0033677 A1 | 2/2008 | Tomaney | |
| 2008/0154512 A1 | 6/2008 | Leong | |
| 2009/0035779 A1 | 2/2009 | Kurnik | |
| 2009/0218517 A1 | 9/2009 | Bedingham | |
| 2010/0047265 A1 | 2/2010 | Romero | |

FOREIGN PATENT DOCUMENTS

| | | |
|---|---|---|
| CN | 1262833 | 7/2006 |
| CN | 1354361 | 7/2006 |
| DE | 2021654 | 10/1971 |
| DE | 2055944 | 5/1972 |
| GB | 1599452 | 10/1981 |
| JP | 61020839 | 1/1986 |
| WO | WO 9103915 | 3/1991 |
| WO | WO 9838510 | 9/1998 |
| WO | WO 0101112 | 1/2001 |
| WO | WO 0200347 | 1/2002 |
| WO | WO 0201180 | 1/2002 |
| WO | WO 0201181 | 1/2002 |
| WO | WO 02073605 | 9/2002 |
| WO | WO 03057369 | 7/2003 |
| WO | WO 03058253 | 7/2003 |
| WO | WO 03098278 | 11/2003 |
| WO | WO 03098279 | 11/2003 |
| WO | WO 03102226 | 12/2003 |
| WO | WO 2004079343 | 9/2004 |
| WO | WO 2004087950 | 10/2004 |
| WO | WO 2005030395 | 4/2005 |
| WO | WO 2006107619 | 10/2006 |
| WO | WO 2006107627 | 10/2006 |
| WO | WO 2011031585 | 3/2011 |

OTHER PUBLICATIONS

Daubechies, "The Wavelet Transform, Time-Frequency Localization and Signal Analysis", IEEE Transactions on Information Theory, vol. 36, No. 5, pp. 961-1005, (Sep. 1990).

"Dye", Definition of dye from Merriam-Webster Online Dictionary, [retrieved from the internet on Dec. 10, 2007], <http://www.m-w.com/dictionary/dye>, 1 page.

Lee, "A Novel Real-Time PCR Machine with a Miniature Spectrometer for Fluorescence Sensing in a Micro Liter Volume Glass Capillary", Sensors and Actuators, B 100, pp. 401-410, (2004).

Lee, "Development of a CCD-Based Fluorimeter for Real-Time PCR Machine", Sensors and Actuators, B 107, pp. 872-881 (2005).

Torrence, "A Practical Guide to Wavelet Analysis", Bulletin of the American Meteorological Society, vol. 79, No. 1, pp. 61-78, (Jan. 1998).

Verwer, "BD FACSDiVa Option", White Paper, pp. 1-19, (2002), http://www.bdbioschiences.com/ecat/documentSearch.do?key=verwer&prodCount=0&charset=utf-&Match AiiTerms=true, [last visited Oct. 8, 2010.].

Wenner; "Biosensing on the CD Microfluidic Platform with Genetically Engineered Proteins", Society of Automotive Engineers, Inc., 2000-01-2513, pp. 1-6, (2000).

Search Report for PCTUS2006-010787, 4 pages.
Written Opinion for PCTUS2006-010787, 6 pages.
Search Report for PCTUS2006-010978, 4 pages.
Written Opinion for PCTUS2006-010978, 6 pages.
Search Report for PCTUS2009-41656, 3 pages.
Written Opinion for PCTUS2009-41656, 12 pages.
Search Report for PCTUS2010-47265, 2 pages.
Written Opinion for PCTUS2010-47265, 8 pages.
U.S. Appl. No. 60/260,063.
U.S. Appl. No. 60/284,637.

* cited by examiner

ANALYSIS OF NUCLEIC ACID AMPLIFICATION CURVES USING WAVELET TRANSFORMATION

CROSS REFERENCE TO RELATED APPLICATIONS

This application is a national stage filing under 35 U.S.C. 371 of PCT/US2009/041656, filed Apr. 24, 2009, which claims priority to U.S. Provisional Application No. 61/047,606, filed Apr. 24, 2008, the disclosure of which is incorporated by reference in its/their entirety herein.

TECHNICAL FIELD

The disclosure relates to techniques for analyzing nucleic acid amplification curves.

BACKGROUND

Nucleic acid analyses can be used for sequencing, cloning, genetic mapping, and other forms of nucleic acid sequence analysis, or to determine an initial concentration of nucleic acid in a sample by constructing a standard curve of results from samples including known concentrations. Nucleic acid analyses can be used to analyze nucleic acids including, for example, DNA and RNA. Types of nucleic acid analysis include polymerase chain reaction (PCR), transcription mediated amplification (TMA), ligase chain reaction (LCR), strand-displacement amplification (SDA) and nucleic acid sequence based amplification (NASBA).

In general, PCR relies on the ability of DNA-copying enzymes to remain stable at high temperatures. A single PCR cycle includes three major steps: denaturation, annealing, and extension. During the denaturation, a liquid sample is heated at approximately 94° C. During this process, double DNA strands "melt" open into single stranded DNA and all enzymatic reactions stop. During annealing, the single stranded DNA is cooled to 54° C. At this temperature, primers bind or "anneal" to the ends of the DNA strands. During extension, the sample is heated to 75° C. At this temperature, nucleotides add to the primers and eventually a complementary copy of the DNA template is formed. PCR analyses typically repeat this PCR cycle multiple (e.g., about 40) times to produce a large number of replicate DNA strands.

Real-time PCR can be used to detect a relative amount of nucleic acid present in a sample as the sample undergoes a plurality of PCR cycles. For example, the sample may include markers that fluoresce when attached to double-stranded DNA. In this example, fluorescence detected by a detector is proportionate to the number of double-stranded DNA present in the sample. Thus, as PCR proceeds, fluorescence increases.

SUMMARY

In general, the disclosure is directed to a new analysis method for real-time nucleic acid amplification based on a wavelet transform. That is, techniques are described for analyzing nucleic acid amplification data, which may be represented as an amplification curve, using wavelet transformation. Wavelet transformation generally transforms a data set from a time domain to a time-frequency domain. When applied to real-time nucleic acid amplification data, in which intensity data is collected for a plurality of amplification cycles, the wavelet transformation transforms the amplification data from a cycle domain into a cycle-frequency domain. Wavelet transformation may be used as an aid in identifying a cycle corresponding to a point within a growth period of the amplification data, which is referred to herein as a $T_{max}$ value for the data. For example, the wavelet transformation is a cycle-frequency representation of the amplification curve, which in general has a complicated time dependence. After performing the wavelet transform, the $T_{max}$ value may be identified as a cycle within the transformed amplification data at which one or more frequency components of the transformed amplification data have a local maximum magnitude.

The techniques may be applied to determine an amount of nucleic acid present within an unknown sample. For example, the $T_{max}$ values determined based on application of the wavelet transform to the amplification data for a plurality of samples having different known initial concentrations of the same nucleic acid may first be used to construct a standard curve of the $T_{max}$ value of the sample versus a logarithm of the initial nucleic acid concentration of the sample. This standard curve may then be used to determine an unknown initial concentration of a sample of the same nucleic acid. Further, the standard curve may be used to determine an efficiency of the PCR reaction.

In one aspect, the disclosure is directed to a method including performing a PCR analysis of a nucleic acid sample. The PCR analysis includes a plurality of PCR cycles. The method also includes acquiring from the PCR analysis, amplification data proportional to an amount of nucleic acid present for each of the plurality of PCR cycles. The method further includes applying wavelet transformation to the amplification data to determine a PCR cycle corresponding to a point within a growth period of the amplification data, and updating a display based on the PCR cycle corresponding to a point within a growth period of the amplification data.

In another aspect, the disclosure is directed to a computer-readable medium including instructions that cause a processor to initiate a PCR analysis of a nucleic acid sample. The PCR analysis comprises a plurality of PCR cycles. The computer-readable medium also includes instructions that cause the processor to acquire from the PCR analysis, amplification data proportional to an amount of nucleic acid present for each of the plurality of PCR cycles and apply wavelet transformation to the amplification data to determine a PCR cycle corresponding to a point within a growth period of the amplification data. The computer-readable medium further includes instructions that cause the processor to update a display based on the PCR cycle corresponding to a point within a growth period of the amplification data.

In yet another aspect, the disclosure is directed to a device including a control module, an analysis module and an interface module. The control module initializes a PCR analysis of a nucleic acid sample and receives amplification data proportional to an amount of nucleic acid present for each of a plurality of PCR cycles. The analysis module applies wavelet transformation to the amplification data to determine a PCR cycle corresponding to a point within a growth period of the amplification data. The interface module updates a display based on the PCR cycle corresponding to a point within a growth period of the amplification data.

The details of one or more embodiments of the invention are set forth in the accompanying drawings and the description below. Other features, objects, and advantages of the invention will be apparent from the description and drawings, and from the claims.

DETAILED DESCRIPTION

In general, the present disclosure is directed to techniques for analyzing nucleic acid amplification data using wavelet transformation. In one aspect, the present disclosure is directed to applying wavelet transformation to amplification data collected in nucleic acid analyses. In some embodiments, the wavelet transformation comprises continuous wavelet transformation (CWT). In other embodiments, the wavelet transformation comprises discrete wavelet transformation (DWT). While the following description is generally directed to applying wavelet transformation to real-time PCR amplification data, it will be understood that the techniques described herein may be applied to data collected by other nucleic acid analyses, such as, for example, nucleic acid sequence based amplification (NASBA), transcription mediated amplification (TMA), ligase chain reaction (LCR), strand-displacement amplification (SDA), and the like.

Figure 1:
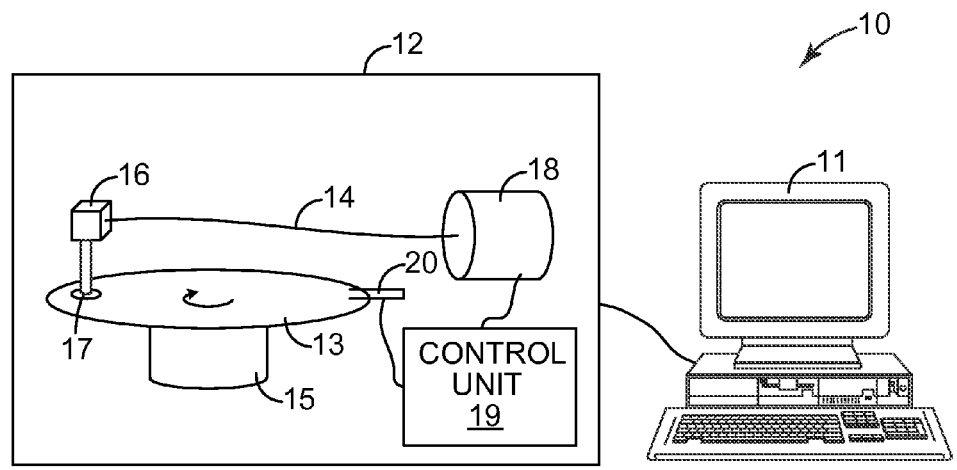
FIG. 1 is a block diagram illustrating an example embodiment of a PCR analysis system.

FIG. 1 is a block diagram illustrating an exemplary embodiment of a PCR analysis system 10 including a data analysis device 11 and a fluorescence detection device 12. System 10 collects PCR amplification data from at least one nucleic acid sample and analyzes the amplification data using wavelet transformation to identify a cycle corresponding to a point within a growth period of the amplification data for the sample. Wavelet transformation generally transforms a data set from a time domain to a time-frequency domain. When applied to PCR amplification data, in which intensity data is collected for a plurality of cycles, the wavelet transformation transforms the amplification data from the cycle domain into a cycle-frequency domain. In some embodiments, the identified cycle corresponds to approximately the onset of the growth period. This cycle may generally correspond to a threshold cycle ($c_t$) in some amplification curve analyses, but will be referred to herein as a $T_{max}$ value indicating that the cycle has been identified by application of wavelet transformation. In general, real-time analysis of PCR amplification data, as described herein, may assist a user in determining an initial concentration of nucleic acid in a sample or an efficiency of a PCR reaction.

Data analysis device 11 provides an operating environment having hardware and software for controlling the operation of fluorescence detection device 12, including control unit 19, optical module 16 and detector 18, to detect a fluorescent dye in a sample 17. In particular, a user interacts with data analysis device 11 to initiate nucleic acid analysis of one or more samples contained within one or more chambers of rotating disk 13 under control of control unit 19. In response, optical module 16 of detection device 12 excites a region of rotating disk 13 and collects emitted fluorescent light energy from a dye contained within the chambers. Disk 13 is mounted on a rotating platform 15. Control module 19 controls rotating platform 15 by engaging a motor associated with the rotating platform 15 to spin disk 13 at a controlled speed.

Optical module 16 interrogates sample 17 and collects fluorescent light energy as the disk 13 rotates. For example, an excitation source within module 16 may be activated for periods sufficient to collect data for each PCR cycle. In one embodiment, the excitation source within optical module 16 is activated for an initial period of approximately two seconds to reach steady state followed by an interrogation period that lasts for 10-50 rotations of disk 13. In other embodiments, the excitation source may be activated for shorter (e.g., approximately 1 or 2 milliseconds) or longer periods.

Although a single sample 17 is illustrated in FIG. 1, disk 13 may contain a plurality of chambers holding samples. Optical module 16 may interrogate some or all of the different chambers of disk 13. In one embodiment, disk 13 includes 96 chambers spaced around a circumference of disk 13. With a 96-chamber disk, system 10 may be capable of acquiring data from 96 samples, each comprising a similar or different initial concentration of nucleic acid. Additionally, in some embodiments, system 10 may be capable of acquiring data concurrently from samples including different nucleic acids and/or different fluorescent dyes.

In one embodiment, optical module 16 includes at least one excitation source that is an inexpensive high power light emitting diode (LED). LEDs are commercially available in a variety of wavelengths and have long lifetimes (e.g., 100,000 hours or more). In another embodiment, a conventional halogen bulb or mercury lamp may be used as an excitation source.

As illustrated in FIG. 1, optical module 16 may be coupled to a fiber optic cable 14. Fiber optic cable 14 provides a flexible mechanism for collection of fluorescent signals from optical module 16 without loss of sensitivity. In this example, fiber optic cable 14 couples optical module 16 to a detector 18. The fiber optic cable 14 carries the fluorescent light collected by optical module 16 and effectively delivers the captured light to detector 18. In one embodiment, detector 18 is a photomultiplier tube. In other embodiments, one or more solid-state detectors may be used.

Optical module 16 may be removable from the device and easily interchangeable with other optical modules that are optimized for interrogation at different wavelengths. The modular architecture of system 10 allows the device to be easily adapted for all of the fluorescent dyes used in a given analysis environment, such as PCR. Other chemistries that may be used in system 10 include Invader® (Third Wave, Madison, Wis.), Transcription-mediated Amplification (Gen-Probe, San Diego, Calif.), fluorescence labeled enzyme linked immunosorbent assay (ELISA) or fluorescence in situ hybridization (FISH). The modular architecture of system 10 may provide another advantage in that the sensitivity of each optical module 16 can be optimized by choice of the corresponding excitation source (not shown) and excitation and detection filters (not shown) for a specific target range of wavelengths in order to selectively excite and detect a corresponding dye in the PCR analysis.

While the system 10 includes a single optical module 16 in the illustrated embodiment, in other embodiments, the system may include a plurality of optical modules 16. For example, in some embodiments, system 10 may include four optical modules 16 that provide four "channels" for optical detection of four different dyes. A system 10 capable of detecting multiple target species in real-time PCR may be referred to as a multiplex PCR system. Each of these four optical modules may excite different regions of rotating disk 13 at any given time and collect emitted fluorescent light energy at different wavelengths from the dyes. In embodiments including multiple optical modules, multiple, parallel reactions occurring within sample 17 may be interrogated substantially simultaneously. In other embodiments including multiple optical modules 16, multiple different reactions occurring in different chambers of disk 13 may be interrogated substantially simultaneously.

Each of the plurality of optical modules may be optically coupled to a fiber optic cable 14 that forms a part of a fiber optic bundle. The fiber optic bundle may optically couple the optical modules to a single detector 18, or to multiple detectors. The use of a single detector 18 may be advantageous in that it allows use of a highly sensitive and possibly expensive detector (e.g., a photomultiplier), while maintaining a minimal cost in that only a single detector need be used.

In the example of FIG. 1, samples 17 are contained in chambers of disk 13, which is mounted on rotating platform 15 under the control of control unit 19. A slot sensor trigger 20 provides an output signal utilized by control unit 19 and data analysis device 11 for synchronizing data acquisition with chamber position during disk rotation. Slot sensor trigger 20 may be a mechanical or optical sensor. For example, the sensor may be a laser that sends a beam of light to disk 13 and control unit 19 uses a sensor detecting light passing through a slot in disk 13 to locate the chambers on the disk. In other embodiments, disk 13 may include a tab, protrusion or reflective surface in addition to or in place of the slot. Slot sensor trigger 20 may use any physical structure or mechanism to locate the radial position of disk 13 as it rotates. Optical module 16 may be physically mounted above rotating platform 15. As a result, optical module 16 overlaps with different chambers at any one time.

Analysis system 10 may also include a heating element (not shown) for modulating the temperature of the sample 17 on disk 13. In one embodiment, the heating element may comprise a cylindrical halogen bulb contained within a reflective enclosure. The reflective enclosure is shaped to focus radiation from the bulb onto a radial section of disk 13. Generally, the heated area of disk 13 would resemble a ring as disk 13 spins. In this embodiment, the shape of the reflective enclosure may be a combination of elliptical and spherical geometries that allow precise focusing of the radiant energy. In other embodiments, the reflective enclosure may be of a different shape or the bulb may broadly irradiate a larger area.

In yet other embodiments, the reflective enclosure may be shaped to focus the radiation from the bulb onto a single area of the disk 13, such as a single process chamber containing a sample 17.

In some embodiments, the heating element may heat air and force the hot air over one or more samples 17 to modulate the temperature. Additionally, the samples 17 may be heated directly by the disk 13. In this case, the heating element may be located in platform 15 and thermally coupled to disk 13. Electrical resistance within the heating element may heat a selected region of the disk 13 as controlled by control unit 19. For example, a region may contain one or more chambers, and possibly the entire disk 13.

Alternatively, or in addition, system 10 may include a cooling component (not shown). A fan may be included in system 10 to supply cold air, e.g., room temperature air, to disk 13. Cooling may be needed to modulate the temperature of the sample appropriately and store samples 17 after an experiment has completed. In other embodiments, the cooling component may include thermal coupling between platform 15 and disk 13, and platform 15 may reduce its temperature when needed. For example, some biological samples may be stored at 4 degrees Celsius to reduce enzyme activity or protein denaturing.

Further details on exemplary apparatuses that can be used in the practice of the present invention may be found in, for example, U.S. Patent Application Publication No. 2006-0223172, entitled "MULTIPLEX FLUORESCENCE DETECTION DEVICE HAVING FIBER BUNDLE COUPLING MULTIPLE OPTICAL MODULES TO A COMMON DETECTOR;" U.S. Pat. No. 7,507,575, entitled "MULTIPLEX FLUORESCENCE DETECTION DEVICE HAVING REMOVABLE OPTICAL MODULES;" U.S. Patent Application Publication No. 2007-0009382, entitled "HEATING ELEMENT FOR A ROTATING MULTIPLEX FLUORESCENCE DETECTION DEVICE;" U.S. Patent Application Publication No. 2007-0009383, entitled "VALVE CONTROL SYSTEM FOR A ROTATING MULTIPLEX FLUORESCENCE DETECTION DEVICE;" and U.S. Patent Application Publication No. 2007-001007, entitled "SAMPLE PROCESSING DEVICE COMPRESSION SYSTEMS AND METHODS." The entire contents of these disclosures are incorporated herein by reference.

For real-time PCR, fluorescence may be used to measure the amount of amplification during a PCR analysis session using one of three general techniques. The first technique is the use of a dye, such as Sybr® Green (Molecular Probes, Eugene, Oreg.), whose fluorescence increases upon binding to double-stranded DNA. The second technique uses fluorescently labeled probes whose fluorescence changes when bound to an amplified target sequence (hybridization probes, hairpin probes, etc.). This technique is similar to using a double-stranded DNA binding dye, but is more specific because the probe will bind only to a certain section of the target sequence. The third technique is the use of hydrolysis probes (Taqman™, Applied BioSystems, Foster City, Calif.), in which the exonuclease activity of the polymerase enzyme cleaves a quencher molecule from the probe during the extension phase of a PCR cycle, making it fluorescently active.

In each of the approaches, the amount of fluorescence is approximately linearly proportional to the amplified nucleic acid concentration. Data analysis device 11 measures an output signal from detector 18 during each PCR cycle (or alternatively optionally sampled, buffered and communicated by control unit 19 after the PCR cycle) to observe the amplification in near real-time. In some embodiments, the control unit 19 or data analysis device 11 may integrate the output signal from detector 18 over a length of a PCR cycle to produce a single fluorescence value for each PCR cycle. In other embodiments, data analysis device 11 may measure and retain a plurality of output signals indicative of fluorescence from detector 18 for each PCR cycle. Data analysis device 11 stores data representative of the output signal(s) for each PCR cycle as amplification data in matrix or table format, where, for example, each column of one row stores the cycle number and the same column of a second row stores the associated fluorescence intensity.

Figure 2:
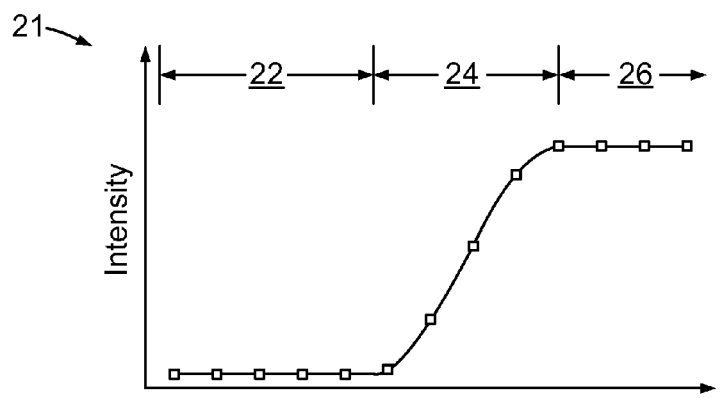
FIG. 2 is PCR amplification curve for an example nucleic acid sample.

Data analysis device 11 may also convert the data from detector 18 for a plurality of PCR cycles in a single PCR analysis session into an amplification curve, such as amplification curve 20 shown in FIG. 2. For a typical PCR analysis session, amplification curve 20 represents the amplification of a sample sensed by fluorescence for each of a plurality of PCR cycles. The amplification curve 20 may include single fluorescence intensity value for each of the plurality of PCR cycles, with a curve fit to the data. The curve may be fit using, for example, linear regression, or may simply connect fluorescence data from adjacent cycles with a smoothed or non-smoothed line. In other embodiments, the amplification curve 20 may include more than one fluorescence intensity value for each of the plurality of PCR cycles. The amplification curve for a single PCR analysis session may generally be divided into approximately three regions: the baseline period 22, the growth period 24 and the plateau period 26.

In accordance with the techniques described herein, data analysis device 11 may apply wavelet transformation to the amplification data or amplification curve 20 to determine a point along the amplification curve, referred to herein as a $T_{max}$ value, which is a PCR cycle corresponding to a point within growth period 24 of the amplification data or amplification curve 20. Specifically, wavelet transformation of the amplification data or amplification curve 20 produces a cycle-frequency representation of the amplification curve 20, which in general has a complicated cycle dependence. After performing the wavelet transform, data analysis device 11 identifies a $T_{max}$ value as a cycle value within the transformed amplification data at which one or more frequency components of the transformed amplification data have the largest magnitude. That is, data analysis device 11 applies wavelet transformation to the amplification data to decompose the amplification data into a series of basis functions (i.e. wavelets). This allows the amplification data to be analyzed so as to identify the larger magnitude frequency components while maintaining the cycle relationship of the components. As a result, data analysis device 11 is able to identify a cycle having the largest local wavelet magnitude for one or more frequency slice within the transformed amplification data and correlate this to a $T_{max}$ value for the PCR analysis session associated with the amplification data. Data analysis device 11 may then update a display based on the $T_{max}$ value.

Figure 3:
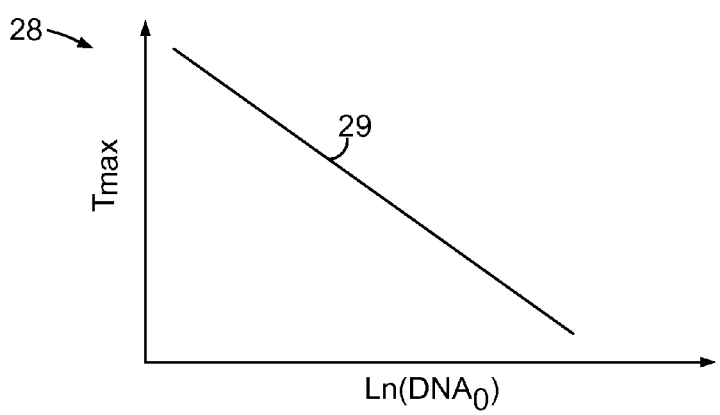
FIG. 3 is a standard curve for an example nucleic acid dilution series.

When system 10 performs PCR on a plurality of samples including different known initial concentrations of a nucleic acid, data analysis device 11 may generate a plot 28 including a standard curve 29 of the $T_{max}$ of the sample versus a logarithm of initial DNA concentration ($DNA_0$), as shown in FIG. 3. The standard curve 29 may include a line fit to a plurality of ($\ln(DNA_0)$, $T_{max}$) data points using linear regression or another curve fitting technique. Data analysis device 11 may subsequently use the standard curve 29 or an equation representative of standard curve 29 to quantify an initial concentration of a nucleic acid sample having an unknown initial concentration of nucleic acid. For example, device 11 may determine a $T_{max}$ value for the sample having an unknown initial concentration of nucleic acid. Device 11 may then plot the $T_{max}$ value along standard curve 29 at a point corresponding to the $T_{max}$ value, or may insert the $T_{max}$ value into the equation of standard curve 29 to determine the initial concentration of nucleic acid in the sample. Data analysis device 11 may also use the standard curve 29 to determine an efficiency of the PCR reaction, as described in further detail below.

Figure 4:
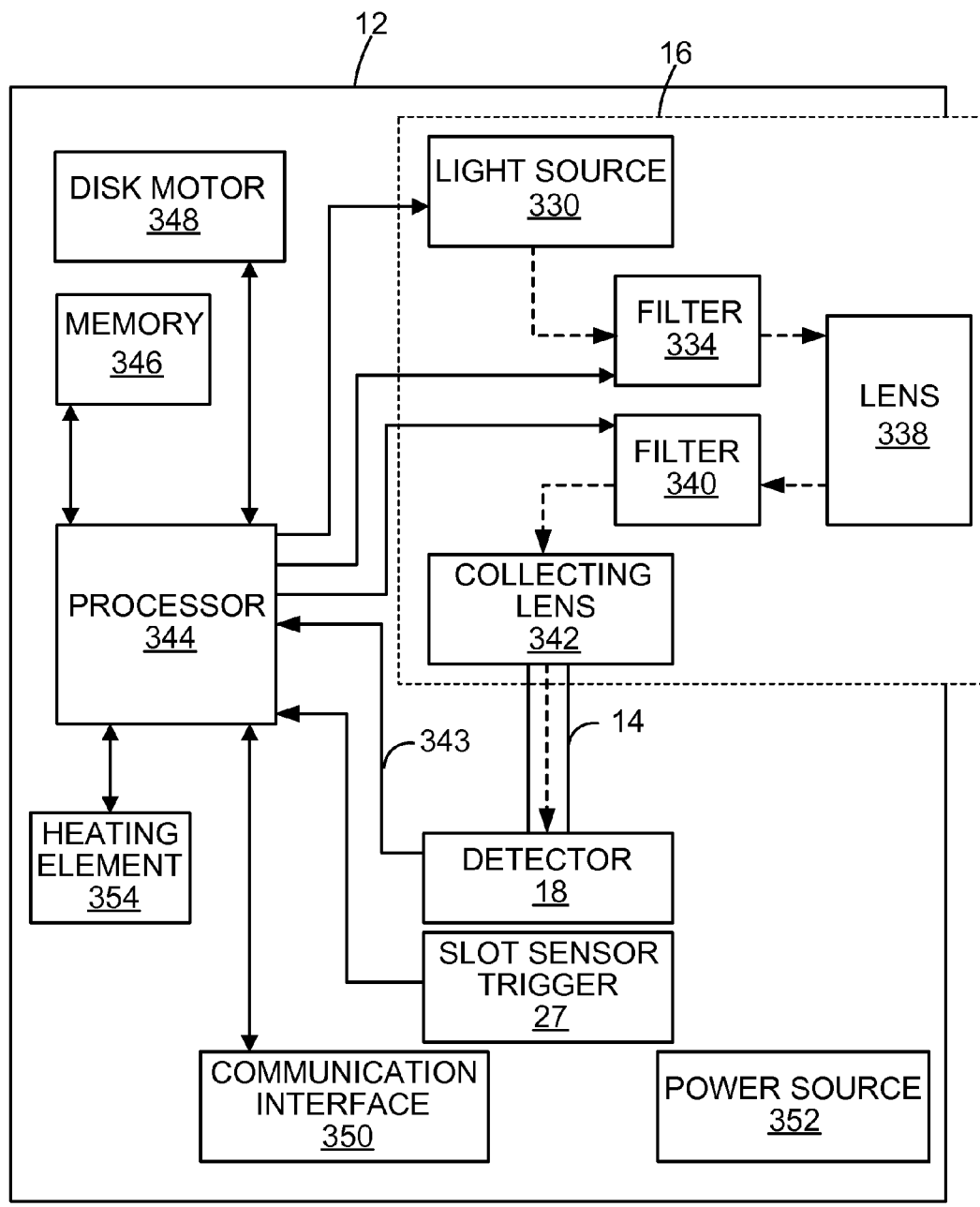
FIG. 4 is a block diagram illustrating an example embodiment of the fluorescence detection device in further detail.

FIG. 4 is a functional block diagram of an example embodiment of fluorescence detection device 12. In particular, FIG. 4 indicates the electrical connections between device components and the general paths of light through the components. In the example of FIG. 4, device 12 includes at least one processor 344 or other control logic, memory 346, disk motor 348, light source 330, excitation filter 334, lens 338, detection filter 340, collecting lens 342, detector 18, slot sensor trigger 27, communication interface 350, heating element 354, laser 355 and power source 352. As shown in FIG. 4, lens 338 and collecting lens 342 need not be electrically connected to another component. Further, light source 330, filters 334 and 340, lens 338 and collecting lens 342 are representative of one optical module 16. Although not illustrated in FIG. 4, device 12 may contain additional optical modules 16, as described previously. In that case, each additional optical module may include components arranged substantially similarly to those shown in FIG. 4.

Light follows a certain path through several components in FIG. 4. Once light is emitted by light source 330, it enters excitation filter 334 and leaves as light of a discrete wavelength. It then passes through lens 338 where it leaves detection device 12 and excites sample 17 within a process chamber (not shown). Sample 17 responds by fluorescing at a different wavelength, at which time this light enters lens 338 and is filtered by detection filter 340. Filter 340 removes background light of wavelengths outside of the desired fluorescence from sample 17. The remaining light is sent through collecting lens 342 and enters fiber optic cable 14 before being detected by detector 18. Detector 18 subsequently amplifies the received light signal.

Processor 344, memory 346 and communication interface 350 may be part of control unit 19. Processor 344 controls disk motor 348 to rotate or spin disk 13 as needed to collect fluorescence information or move fluid through disk 13. Processor 344 may use disk position information received from slot sensor trigger 20 to identify the location of chambers on disk 13 during rotation and synchronize the acquisition of florescence data received from the disk 13.

Processor 344 may also control when the light source 330 within optical module 16 is powered on and off. In some embodiments, processor 344 controls excitation filter 334 and detection filter 340. Depending on the sample being illuminated, processor 344 may change the filter to allow a different wavelength of excitation light to reach the sample or a different wavelength of fluorescence to reach collecting lens 342. In some embodiments, one or both filters may be optimized for the light source 330 of the particular optical module 16 and not changeable by processor 344.

Collecting lens 342 is coupled to fiber optic cable 14, which provides an optical path for the light from collecting lens 342 to detector 18. Processor 344 may control the operation of detector 18. While detector 18 may constantly be detecting all light, some embodiments many utilize other acquisition modes. Processor 344 may determine when detector 18 collects data and may programmatically set other configuration parameters of detector 18. In one embodiment, detector 18 is a photomultiplier tube that captures fluorescence from light provided by collecting lens 342. In response, detector 18 produces an output signal 343 (e.g., an analog output signal) representative of the received light. Although not shown in FIG. 3, in embodiments including a plurality of optical modules, detector 18 may concurrently receive light from other optical modules 16 of device 12. In that case, output signal 343 electrically represents a combination of the optical input received by detector 18 from the various optical modules 16.

Processor 344 may also control data flow from device 12. Data such as sampled fluorescence from detector 18, temperature of the samples from heating element 354 and related sensors, and disk rotation information may be stored into memory 346 for analysis. Processor 344 may comprise any one or more of a microprocessor, digital signal processor (DSP), application specific integrated circuit (ASIC), field-programmable gate array (FPGA), or other digital logic circuitry. Moreover, processor 344 provides an operating environment for firmware, software, or combinations thereof, stored on a computer-readable medium, such as memory 346.

Memory 346 may include one or more memories for storing a variety of information. For example, one memory may contain specific configuration parameters, executable instructions, and one may contain collected data. Therefore, processor 344 may use data stored in memory 346 for controlling device operation and calibration. Memory 346 may include any one or more of a random access memory (RAM), read-only memory (ROM), electronically-erasable programmable ROM (EEPROM), flash memory, or the like.

Processor 344 may additionally control heating element 354. Based upon the instructions contained within memory 346, the heating element 354 may be selectively driven to control the temperature of one or more chambers according to desired heating profiles. Generally, heating element heats one radial section of disk 13 as the disk spins. Heating element 354 may comprise a halogen bulb and reflector for focusing heating energy on a specific area of disk 13. In other embodiments, heating element 354 may heat one or more chambers sequentially. This embodiment would require disk 13 to be stationary while a chamber is heated. In any embodiment, heating element 354 may be capable of turning on and off extremely quickly as needed.

Processor 344 utilizes communication interface 350 to communicate with data analysis device 11. The communication interface 350 may include a single method or combination of methods to transfer data. Some methods may include a universal serial bus (USB) port or IEEE 1394 port for hardwire connectivity with high data transfer rates. In some embodiments, a storage device may be directly attached to one of these ports for data storage for post processing. The data may be pre-processed by processor 344 and ready for viewing, or the raw data may need to be completely processed before analyzing can begin.

Communications with analysis device 11 may also be accomplished by radio frequency (RF) communication or a local area network (LAN) connection. Moreover, connectivity may be achieved by direct connection or through a network access point, such as a hub or router, which may support wired or wireless communications. For example detection device 12 may transmit data on a certain RF frequency for reception by the target data analysis device 11.

In addition, detection device 12 may be able to download updated software, firmware, and calibration data from a remote device over a network, such as the internet. Communication interface 350 may also enable processor 344 to monitor, inventory and report any failures. If operational problems occur, processor 344 may be able to output error information to assist a user in trouble shooting the problems by providing operational data. For example, processor 344 may provide information to help the user diagnose a failing heating element or a synchronization problem.

Power source 352 delivers operating power to the components of device 12. Power source 352 may utilize electricity from a standard 115 Volt electrical outlet or include a battery and a power generation circuit to produce the operating power. In some embodiments, the battery may be rechargeable to allow extended operation. For example, device 12 may be portable to detection of biological samples in an emergency, such as a disaster area. Recharging may be accomplished through the 115 Volt electrical outlet. In other embodiments, traditional batteries may be used.

Figure 5:
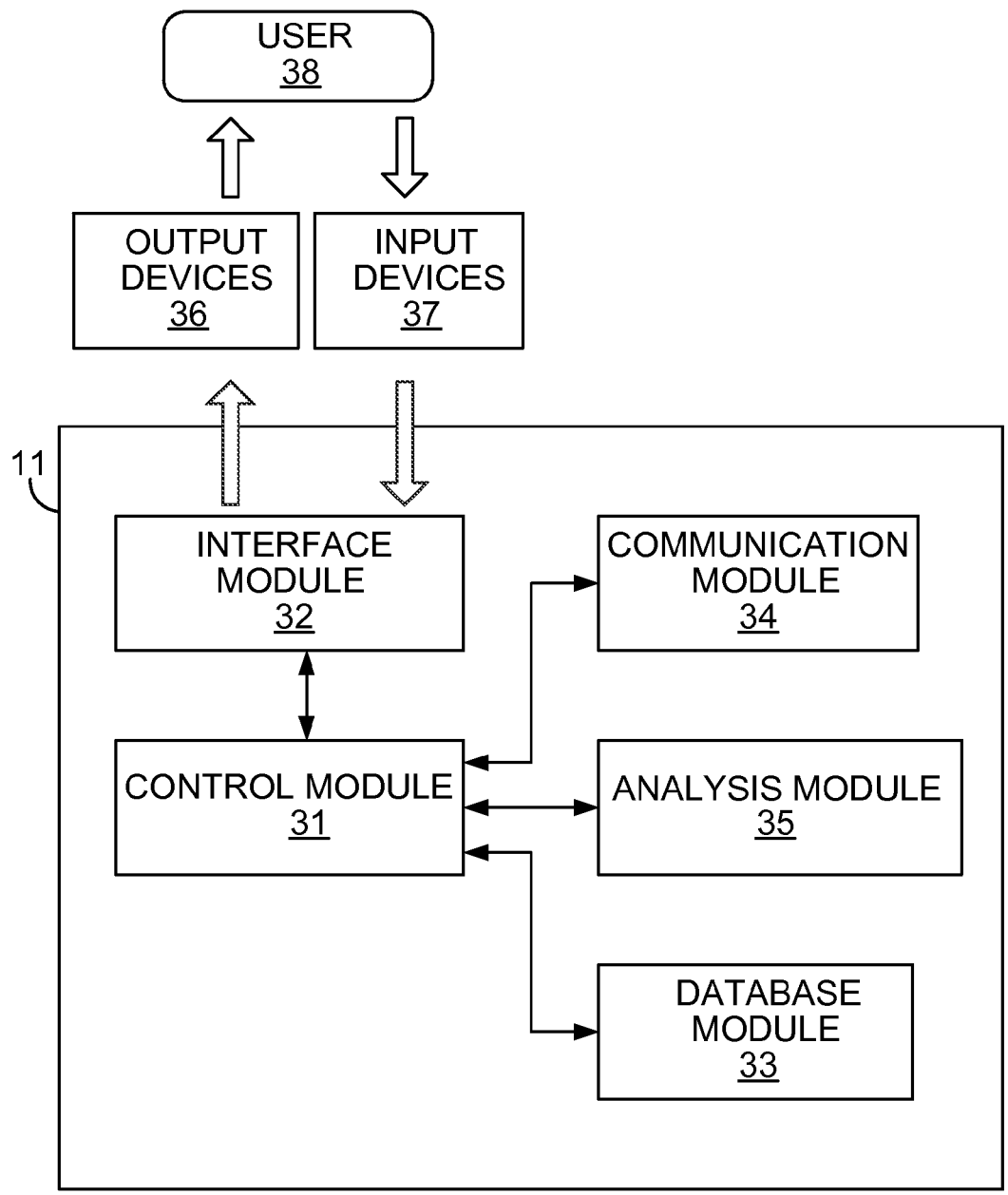
FIG. 5 is a functional block diagram illustrating an example data analysis device.

FIG. 5 is a functional block diagram illustrating further details of an exemplary data analysis device 11, which may be a general computing device, such as a desktop computer, executing software on one or more microprocessors. In the illustrated embodiment, data analysis device 11 may be viewed functionally as including a control module 31, an interface module 32, a database module 33, a communication module 34, and an analysis module 35.

Interface module 32 represents software and hardware necessary for interacting with a user, e.g., for receiving input from a user 38 and for outputting information to the user 38. Interface module 32 may receive input from input devices 37 and output data to output devices 36 that enable a user to interact with system 10. For example, user 38 may change operational parameters of detection device 12 and analysis device 11 and manipulate data stored in database module 33. Moreover, user 38 may interact with interface module 32 to initiate real-time nucleic acid amplification of samples 17 stored within chambers of disk 13. Further, user 38 may interact with data analysis device 11 to view and manipulate the acquired data. During this process, interface module 32 may present a user with user interface screens for interacting with analysis device 11, including, for example, the exemplary user interface screens shown in FIGS. 13-22. Exemplary input devices 37 include a keyboard, a touchscreen, a mouse, a microphone, and the like. Output devices 38 may include, for example, an LCD screen, an LED array, a CRT screen, or a touchscreen display.

Control module 31 represents control logic that, in response to input received from user 38 via interface module 32, directs the operation of fluorescence detection device 12. For example, control module 31 may comprise software instructions that, when executed, provide control logic for communicating commands to control unit 19 of fluorescence detection device 12 to commence PCR analysis and data collection. Moreover, control module 31 may provide commands to request and receive buffered amplification data from control unit 19 during or upon completion of each PCR cycle or PCR analysis session. Furthermore, control module 31 provides control logic for storing the buffered amplification data within database module 33, and for invoking analysis module 35 to process the data in response to commands from user 38.

Analysis module 35 receives amplification data from control module 31, processes the amplification data using wavelet transformation and determines a $T_{max}$ value for a PCR analysis session of one or more PCR cycles associated with the amplification data. For example, analysis module 35 applies wavelet transformation to the amplification data to identify the PCR cycle corresponding to a point within the growth period of the amplification data, i.e., the $T_{max}$ value for the curve. In some embodiments, the PCR cycle may correspond to an approximate onset of the growth period, may correspond to the termination of the growth period, or may correspond to some other point within the grown period. In some embodiments, the analysis module 35 may determine the $T_{max}$ value for a PCR analysis session to a fraction of a cycle.

In addition, analysis module 35 may optionally allow user 38 to select and apply a manual or automatic threshold technique to identify a cycle (e.g., threshold cycle, $c_t$) corresponding to a point within a growth period of the amplification data. The manual threshold technique relies on a user to set a threshold fluorescence intensity. The analysis module 35 then determines when the amplification data crosses this threshold and returns the cycle at which this occurs as the $c_t$ value.

If the automatic threshold technique is selected, analysis module 35 automatically determines a threshold fluorescence intensity. For example, the analysis module 35 may determine an average and a standard deviation of the fluorescence signal in the baseline region of the amplification curve. The analysis module 35 may then set the threshold a certain number of standard deviations above the average baseline fluorescence signal, such as, for example, five standard deviations above the average fluorescence signal. The threshold techniques are described in further detail in U.S. Patent Application Publication No. 2003/0044826, entitled "AUTOMATIC THRESHOLD SETTING FOR QUANTITATIVE POLYMERASE CHAIN REACTION," which is incorporated herein by reference in its entirety. In other embodiments, analysis module 35 may also allow user 38 to choose a derivative technique as a different mechanism for determining a cycle corresponding to a point within a growth period of the amplification data.

In the derivative technique, the analysis module 35 may compute an $n^{th}$ order derivative of the amplification data, determine a maximum, minimum, or zero value of the $n^{th}$ order derivative, and output the PCR cycle at which this value of the derivative is found as the $c_t$ value. The derivative techniques are described in further detail in U.S. Patent Application Publication No. 2002/0028452, entitled "METHOD FOR QUANTIFICATION OF AN ANALYTE," which is incorporated herein by reference in its entirety.

Analysis module 35 may also allow user 38 to choose other techniques as a mechanism for determining a cycle corresponding to a point within a growth period of the amplification data. Other techniques include a fourier transform of the amplification growth curve, as described in further detail in U.S. Patent Application Publication No. 2006/0286587, which is incorporated herein by reference in its entirety; and a Levenberg-Marquardt regression process as described in further detail in U.S. Patent Application Publication No. 2007/0143385, entitled "METHOD FOR QUANTIFICATION OF AN ANALYTE," which is incorporated herein by reference in its entirety.

When wavelet transformation is applied to the amplification data to determine the $T_{max}$ value, the amplification data is decomposed into series of basis functions (i.e. wavelets), which can be a wide variety of functions. One example of a basis function is a Morlet wavelet. Other useful wavelets include, for example, a Haar wavelet, or boxcar function; a Marr wavelet, or Mexican hat; a Paul wavelet; a Daubechies wavelet; a Mathieu wavelet; a Legendre wavelet; a Beta wavelet; a Hermetian wavelet; a Shannon wavelet; a derivative of Gaussian function; or the like.

In general, analysis module 35 applies wavelet transformation to the amplification data to produce a three-dimensional representation of the data, where one dimension is cycle, a second dimension is dilation (e.g., inverse frequency), and a third dimension is the wavelet magnitude. This allows the amplification curve to be analyzed along the cycle and frequency dimensions so as to identify the larger magnitude components while maintaining cycle relationship of the components. As a result, analysis module 35 is able to identify the components having the largest wavelet magnitudes and, based on the cycle relationship of those components, correlate those components to points in the amplification curve indicative of the growth region. For example, based on the magnitudes and their cycle correlation, analysis module 35 is able to identify the $T_{max}$ value for a PCR analysis session associated with the amplification data.

For example, when applying wavelet transformation, analysis module 35 decomposes the amplification data into translations and dilations of the selected wavelet, where each time translation value represents a cycle offset within the amplification data and each dilation value represents a different inverse frequency of the wavelet. Analysis module 35 may do so by multiplying a function representing the amplification data (e.g., an amplification curve) by the selected wavelet evaluated at a time translation value and a dilation value, or by applying the selected wavelet evaluated at a time translation value and a dilation value directly to the amplification data. The analysis module 35 then integrates the resulting function over all cycles to generate a magnitude for the wavelet transformation at that time translation value and dilation value. Analysis module 35 may then increment the time translation value while maintaining the dilation value, carry out the multiplication of the amplification function and the wavelet, and integrate the resulting function to determine a magnitude of the wavelet transformation at this time translation value and dilation value. Analysis module 35 may repeat this process for each time translation and dilation pair so as to create to three-dimensional cycle-frequency-magnitude representation of the amplification data for the selected wavelet.

Analysis module 35 may then utilize the constructed three-dimensional representation so as to identify the $T_{max}$ value for a PCR analysis session, and/or may output the wavelet transformation magnitudes as a graph, text, table, image or the like, as described in further detail below. In one embodiment, analysis module 35 constructs a two-dimensional image in which a first axis is time translation, a second axis is dilation, and a color, shade or intensity of the image at each time translation-dilation coordinate represents the magnitude of the wavelet transformation at that point. In other embodiments, for example, analysis module 35 may construct a three-dimensional graph in which a first axis is time translation, a second axis is dilation, and a third axis is the magnitude of the wavelet transformation. Interface module 32 may display the output of analysis module 35 to a user as an aid to analysis of a PCR session.

As described in further detail below, analysis module 35 may determine a $T_{max}$ value for the amplification data once the wavelet transformation of the amplification data is calculated. For example, analysis module 35 may select a dilation value and determine at which time translation value a local maximum wavelet transformation magnitude occurs for this dilation value. Analysis module 35 may select this local maximum wavelet transformation magnitude according to certain criteria, including, for example, ignoring edge artifacts, such as those that occur from the use of a limited number of dilation values. The time translation value at which the local maximum wavelet transformation magnitude occurs is the $T_{max}$ value for this dilation slice. In some embodiments, analysis module 35 may select a prescribed dilation value (e.g., a frequency slice, described below) at which to determine the $T_{max}$ value. In other embodiments, analysis module 35 may be instructed to select a certain dilation value by a user via interface module 32, or may select more than one dilation value at which to determine the $T_{max}$ value. In this embodiment, analysis module 35 may average the $T_{max}$ values determined for each dilation value to determine an average $T_{max}$ value.

Interface module 32 may then display the $T_{max}$ value on a display of output devices 36. Interface module 32 may display the $T_{max}$ value as text, as a data point on a graph, as part of a table, or the like. In some embodiments, the $T_{max}$ value comprises one point of a standard curve of $T_{max}$ value versus a logarithm of an initial nucleic acid concentration.

In other embodiments, interface module 32 may display a message based on the $T_{max}$ value on a display of output device 36. For example, analysis module 35 may interpret the determination of a $T_{max}$ value to simply mean that a certain nucleic acid is present in the sample that has undergone PCR analysis. Interface module 32 may then display a message indicating the presence of this nucleic acid segment in the sample. Conversely, if a $T_{max}$ value is not determined for the sample (i.e., no amplification has occurred), analysis module 35 may interpret this to indicate that no nucleic acid with a certain sequence is present in the sample, and interface module 32 may display a corresponding message.

In other embodiments, when a sample includes an unknown initial concentration of known nucleic acid, analysis module 35 may determine the $T_{max}$ value for the unknown sample, apply a standard curve for the known nucleic acid, and display the concentration of the unknown sample without displaying the $T_{max}$ value.

In some embodiments, analysis module 35 or control module 31 may apply data preparation techniques, such as curve smoothing, noise reduction, or the like prior to analyzing the amplification data using wavelet transformation.

Data analysis device 11 may be a general-purpose workstation, desktop computer, laptop computer, a handheld computing device, a personal digital assistant (PDA), or other computing device. Data analysis device 11 may include a microprocessor, digital signal processor (DSP), field programmable gate array (FPGA), application specific integrated circuit (ASIC) or other hardware, firmware and/or software for implementing the techniques. In other words, the analysis of PCR amplification data, as described herein, may be implemented in hardware, software, firmware, combinations thereof, or the like. If implemented in software, a computer-readable medium may store instructions, i.e., program code, that can be executed by a processor or DSP to carry out one or more of the techniques described above. For example, the computer-readable medium may comprise magnetic media, optical media, random access memory (RAM), read-only memory (ROM), non-volatile random access memory (NVRAM), electrically erasable programmable read-only memory (EEPROM), flash memory, or other media suitable for storing program code.

Figure 6:
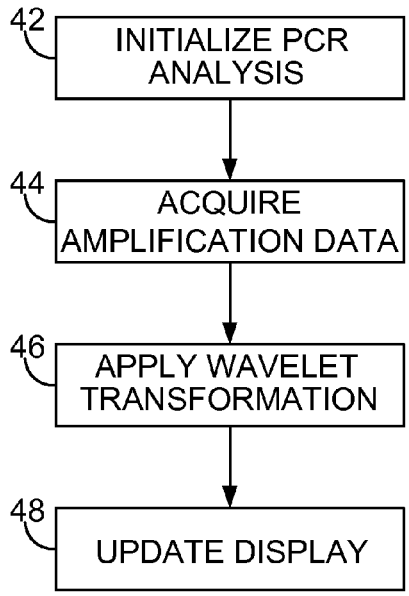
FIG. 6 is a flow diagram illustrating an example operation of a PCR analysis system.

FIG. 6 is a flow diagram illustrating an exemplary method by which data analysis device 11 collects and analyzes PCR amplification data. First, analysis device 11 initializes the PCR analysis (42). For example, analysis device 11 (e.g., control module 31) controls the operation of fluorescence detection device 12 according to parameters stored in database module 33 or input by a user via interface module 32. The parameters may include, for example, sample type and number, fluorescent marker type, detector wavelength, cycle number, cycle steps, cycle temperature profiles and temperature ramp rates, disk rotation speeds, fluorescence detection times, and the like. Analysis device 11 initializes the PCR analysis by, for example, outputting commands to control unit 19 directing fluorescence detection device 12 to prepare for a new PCR analysis session based on the operating parameters specified by the user. In addition, analysis device 11 may initialize one or more files for storage of amplification curve data to be received from fluorescence detection device 12.

In response, control unit 19 acquires PCR amplification data (44) using optical module 16 and detector 18. The control unit 19 may acquire fluorescence data for each PCR cycle, and may collect data for a certain length of time, such as, for example, a certain number of revolutions of disk 13, for each PCR cycle. Control unit 19 may integrate the fluorescence detected by detector 18 to produce a single fluorescence value for each PCR cycle, or may acquire and retain a plurality of fluorescence values for a single PCR cycle. The control unit 19 may buffer the amplification data until the end of the PCR analysis session, or may communicate the data to analysis device 11, which may store the amplification data in database module 33 for later analysis or may transfer the amplification data to analysis module 35 for substantially real-time analysis.

In any case, analysis module 35 of data analysis device 11 applies wavelet transformation to the PCR amplification data (46). As described in further detail below, wavelet transformation transforms the intensity versus cycle amplification data into a frequency-time-based data set that is a function of two new variables: dilation and time translation. For each pair of these new variables, the transformed data has a wavelet transformation magnitude. Based on the transformed data, the analysis module 35 identifies a $T_{max}$ value, which may correspond to the time translation coordinate of a local maximum wavelet transformation magnitude, an average of the time translation coordinates of a plurality of local maximum magnitudes, or may represent another characteristic of the amplification curve selected by a user.

Next, interface module 32 updates a display based on the $T_{max}$ value (48). In some embodiments, the interface module 32 may display the $T_{max}$ value on a graph, as an entry in a table, or in any other suitable format. Further, as described in the context of FIGS. 7 and 8, the $T_{max}$ value may form part of a standard curve, or analysis module 35 may use the $T_{max}$ value to determine an initial nucleic acid concentration in the sample.

In other embodiments, interface module 32 may display a message based on the $T_{max}$ value on a display of output device 36. For example, analysis module 35 may interpret the determination of a $T_{max}$ value to simply mean that a certain nucleic acid segment is present in the sample that has undergone PCR analysis. Interface module 32 may then display a message indicating the presence of this nucleic acid segment in the sample. Conversely, if a $T_{max}$ value is not determined for the sample (i.e., no amplification has occurred), analysis module 35 may interpret this to indicate that no nucleic acid with a certain sequence is present in the sample, and interface module 32 may display a corresponding message. This may be desirable in nucleic acid analyses used to determine the presence of a pathogen, for example.

In other embodiments, when a sample includes an unknown initial concentration of known nucleic acid, analysis module 35 may determine the $T_{max}$ value for the unknown sample, apply a standard curve for the known nucleic acid, and display the concentration of the unknown sample without displaying the $T_{max}$ value.

Figure 7:
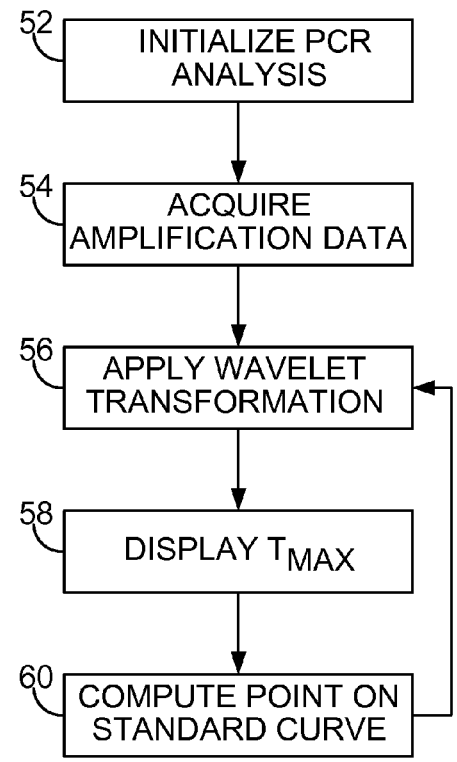
FIG. 7 is a flow diagram illustrating another example operation of a PCR analysis system.

FIG. 7 illustrates another exemplary operation of PCR analysis system 10. Similar to the embodiment described with reference to FIG. 6, control module 31 first initializes fluorescence detection device 12 to begin PCR analysis of a sample (52). In the illustrated embodiment, the sample includes a known initial nucleic acid concentration. Next, control unit 19 of fluorescence detection device 12 acquires amplification data (54) using optical module 16 and detector 18. Analysis module 35 of data analysis 11 then applies wavelet transformation to the amplification data (56) to determine a $T_{max}$ value and displays the $T_{max}$ value (58) using interface module 32. The interface module 32 may display the $T_{max}$ value on a graph, as an entry in a table, or in any other suitable format.

Further, in the embodiment depicted in FIG. 7, analysis module 35 computes and optionally plots a point on a standard curve of $T_{max}$ value versus a logarithm of initial nucleic acid concentration (60). To generate the point on the standard curve, the analysis module 35 or control module 31 calculates a logarithm of the initial nucleic acid concentration in the sample. The analysis module 35 or control module 31 then plots the $T_{max}$ value versus the logarithm of the initial nucleic acid concentration to form one point on the curve. The analysis module 35 may then repeat this procedure for each of a set of samples including the same nucleic acid in different initial concentrations to produce the standard curve. That is, the analysis module 35 may acquire amplification data (54) for each of a plurality of samples that include the same nucleic acid in different initial concentrations and, for each of the samples, apply wavelet transformation (56) to the amplification data of to determine a $T_{max}$ value, calculate a logarithm of the initial nucleic acid concentration, and generate a corresponding point on the standard curve (60). In some embodiments, more than one of the plurality of samples may include the same initial nucleic acid concentration.

The $T_{max}$ value may be approximately linearly proportional to the logarithm of the initial nucleic acid concentration. Thus, a linear regression fit of the data points may be a straight line. Analysis module 35 may use the standard curve, or an equation of the standard curve, to determine an initial concentration of a sample including an unknown initial concentration of the same nucleic acid as that in the samples used to produce the standard curve, as described in further detail with reference to FIG. 8.

Analysis module 35 may also use the equation of the standard curve to determine an efficiency of the PCR reaction. The efficiency of the PCR reaction is a measure of how close the amount of nucleic acid comes to doubling each PCR cycle. The efficiency of the PCR reaction is related to the slope of the curve by the equation:

$$\text{Efficiency} = \frac{(10^{-1/slope})}{2} \times 100\%$$

Thus, simply knowing the slope of the standard curve allows easy calculation of an efficiency for the particular PCR reaction being tested.

Figure 8:
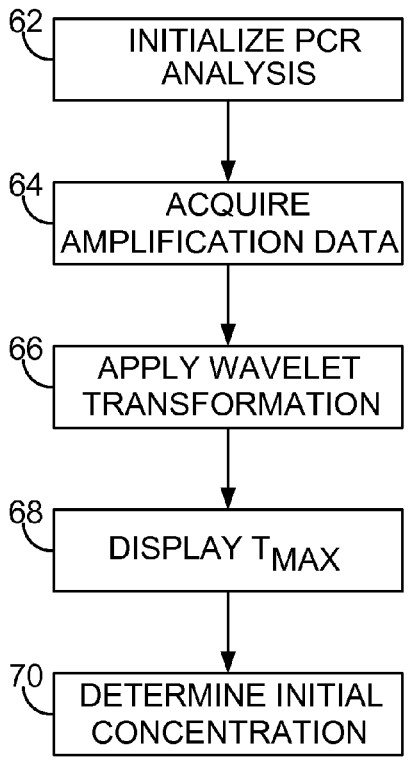
FIG. 8 is a flow diagram illustrating another example operation of a PCR analysis system.

FIG. 8 illustrates yet another exemplary operation of PCR analysis system 10. Similar to the embodiment described with reference to FIGS. 5 and 6, control module 31 first initializes fluorescence detection device 12 to begin PCR analysis of a sample (62). In the embodiment illustrated in FIG. 8, the sample includes an unknown initial concentration of a known nucleic acid. Next, control module 19 of fluorescence detection device 12 acquires amplification data (64) using optical module 16 and detector 18. The analysis module 35 of data analysis 11 then applies wavelet transformation to the amplification data (66) to determine a $T_{max}$ value and displays the $T_{max}$ value (68) using interface module 32. The interface module 32 may display the $T_{max}$ value on a graph, as an entry in a table, or in any other suitable format.

Once the analysis module 35 determines and optionally displays the $T_{max}$ value, the analysis module 35 utilizes a standard curve of the $T_{max}$ values versus a logarithm of the initial concentration for a plurality of samples including the same nucleic acid in different concentrations, or an equation of a standard curve, to determine the initial concentration of the sample (70). The standard curve may be stored in database module 33. In some embodiments, analysis module 35 may generate the standard curve by analyzing amplification data detected from a dilution series of samples including a known initial concentration of a nucleic acid concurrently with the sample including the unknown initial concentration of the same nucleic acid. In other embodiments, the standard curve may have been generated and stored in database module 33 before the PCR analysis session of the unknown sample. Regardless, analysis module 35 may, for example, insert the $T_{max}$ value of the unknown sample into the linear regression equation of the standard curve to calculate the initial nucleic acid concentration in the unknown sample. In other embodiments, analysis module 35 or control module 31 may instruct interface module 32 to display a plot of the $T_{max}$ value on the linear regression line of the standard curve. The analysis module 35 or a user may then determine the initial concentration graphically.

Determining the initial concentration of nucleic acid in an unknown sample may be desirable as an analytical technique, such as, for example, pathogen detection and quantification. For example, a PCR analysis may be performed on a sample that may include a particular pathogen using enzyme and nucleotides for replicating a specific nucleic acid sequence of the pathogen's DNA. If any DNA is amplified, it is then known that the sample contains the pathogen, and an initial amount of the pathogen, or viral load may optionally be determined using the standard curve.

Figure 9:
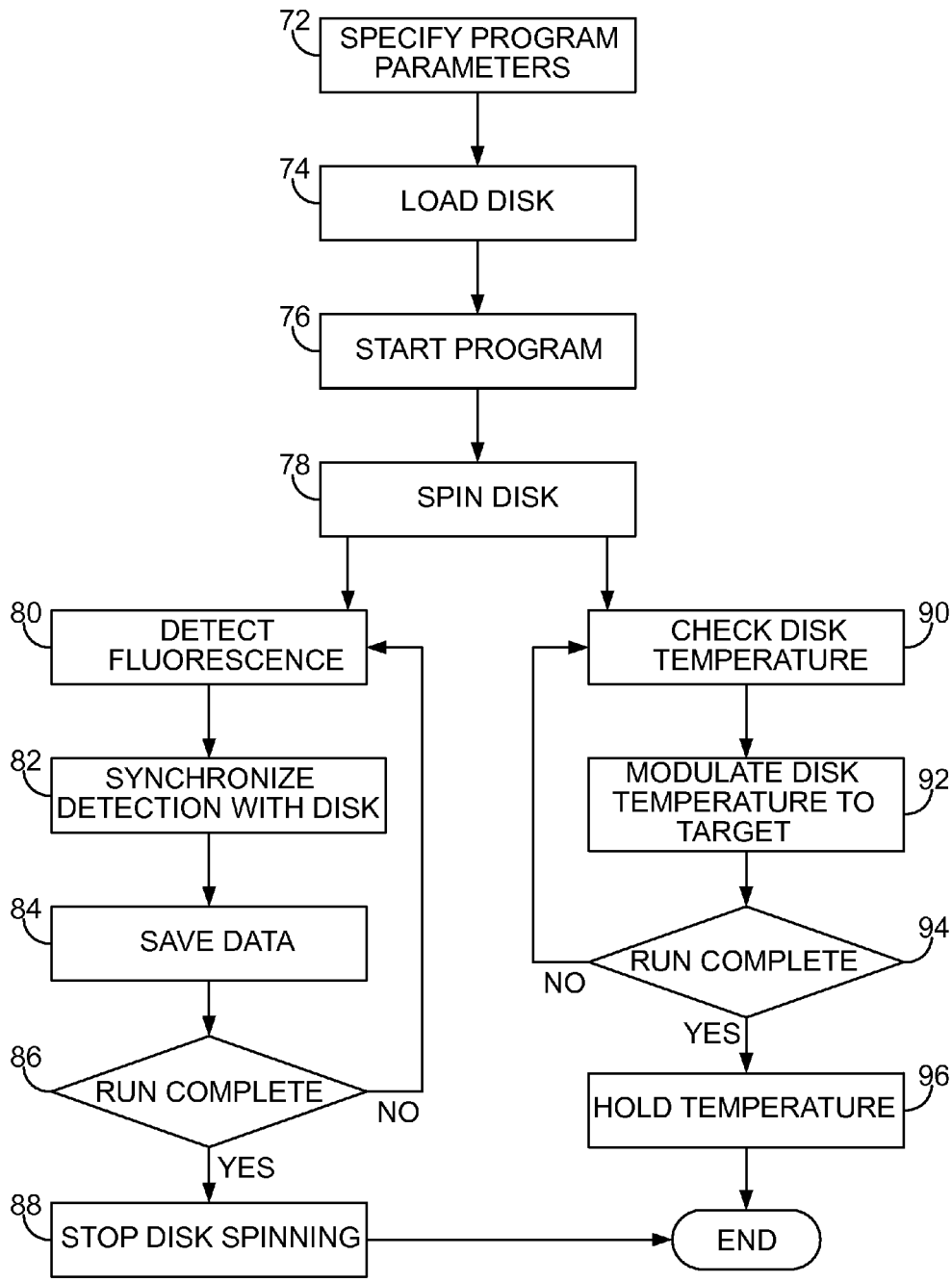
FIG. 9 is a flow diagram illustrating further detail of an example operation of a PCR analysis system.

FIG. 9 is a flow diagram illustrating further detail of an exemplary embodiment of initializing PCR analysis (42, 52, 62) and acquiring amplification data (44, 54, 64) of FIGS. 6-8. Initially, a user specifies program parameters (72) on the data analysis device 11 via input module 32. For example, these parameters may include rotational rates and time periods for rotating disk 13, temperature profiles for each cycle, sample types and sample locations on disk 13, fluorescent marker types, detector wavelengths, and the like.

Next, the user loads disk 13 into the detection device 12 (74). Upon securing the device 12, the user starts the program (session) (76), causing control module 19 to control platform 15 to begin spinning (78) the disk 13 at the specified rate. After the disk 13 has begun to spin, two concurrent processes may occur.

First, the detection device 12 starts to detect fluorescence from the excitation light (80) produced by one or more reactions within one or more samples 17. The detector 18 amplifies the fluorescence signals from each sample 17, which are synchronized to each respective sample 17 and time at which the fluorescence was emitted (82). During this process, control module 19 may transfer the data to data analysis device 11 for substantially real-time analysis (84). Alternatively, control module 19 may buffer the data until the program is complete. The control module 19 continues to measure florescence of the samples and save data until the program is complete (86). Once the run is complete, control module 19 stops the disk 13 from spinning (88).

During this process, control module 19 monitors the disk temperature (90) and modulates the temperature of disk 13, or each sample, to attain the target temperature for that time (92). The control module 19 continues to monitor and control the temperatures until the program is complete (94). Once the run is complete, control module 19 may hold the temperature of the samples to a target storage temperature, usually 4 degrees Celsius (96).

The operation of system 10 may vary from the example of FIG. 7. For example, the disk revolutions per minute may be modified throughout the program. These steps may occur in any order within the operation, depending on the program the user defines.

Figure 10:
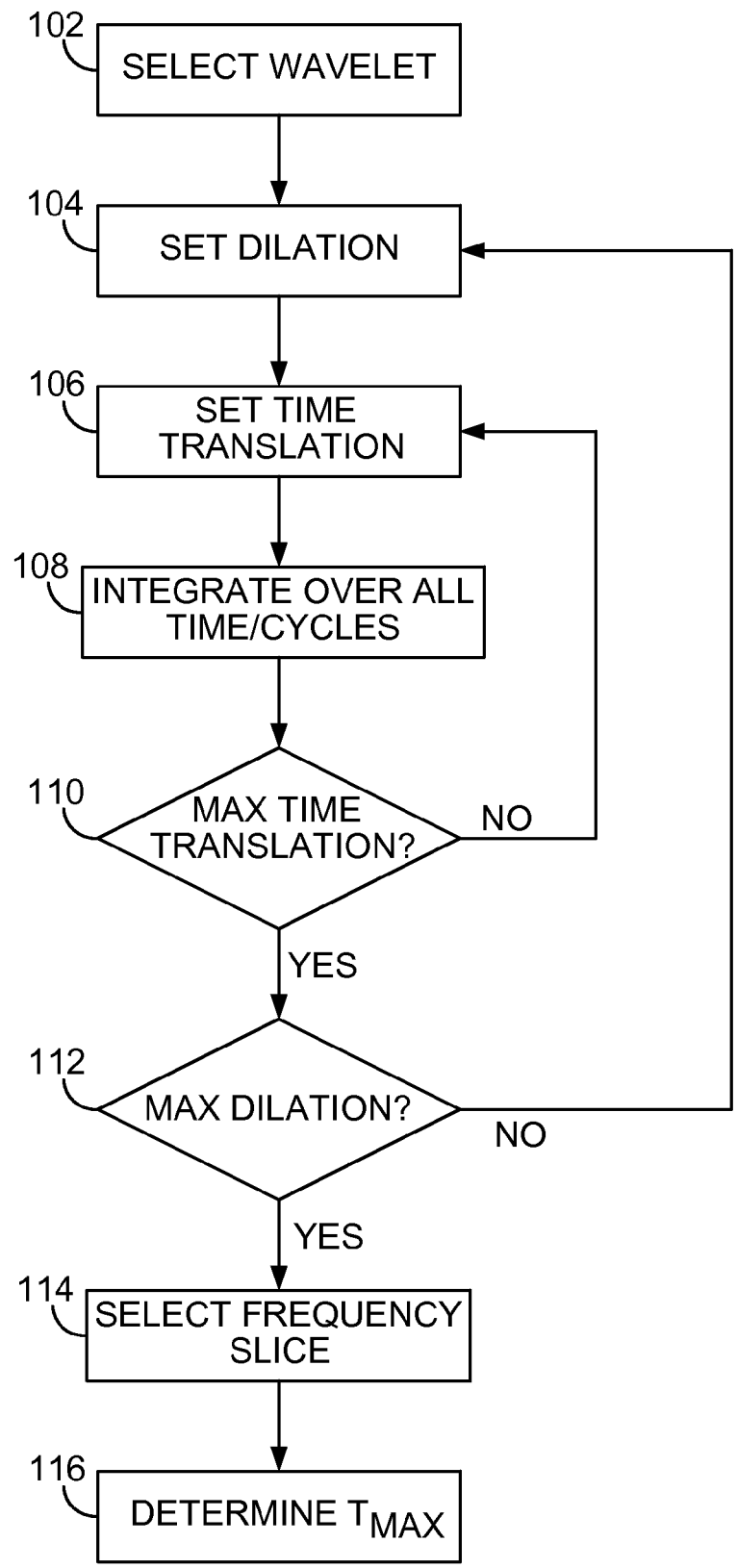
FIG. 10 is a flow diagram illustrating further detail of an example operation of a PCR analysis system.

FIG. 10 is a flow diagram showing further details of an exemplary method of the step applying a wavelet transformation (46, 56, 66) of FIGS. 6-8. While not shown in FIG. 10, analysis module 35 may optionally perform preliminary data manipulations to the amplification data to prepare the data for wavelet analysis. For example, analysis module 35 may connect amplification data points (e.g., one for each PCR cycle) with a line or curve to form an amplification curve. Analysis module 35 may connect amplification data points from adjacent cycles with a line, a smoothed curve, a best fit curve, or the like. Additionally, analysis module 35 may smooth the data to reduce or eliminate noise from the amplification data. In some embodiments, analysis module 35 does not perform preliminary data manipulations on the amplification data.

In the method of FIG. 10, analysis module 35 first selects a wavelet function to apply to the amplification data (102). The wavelet can be any of a wide variety of functions. One common wavelet is a Morlet wavelet:

$$\Psi(t) = \frac{1}{\pi^{1/4}} \cos(\omega t) e^{-t^2/2}$$

where $\omega$ is a frequency and t is time. Another useful wavelet is a Haar wavelet, or boxcar function:

$$\Psi(t) = \begin{cases} 1 & 0 \leq t < 0.5 \\ -1 & 0.5 \leq t < 1 \\ 0 & \text{elsewhere} \end{cases}$$

where t is time. Another useful wavelet is a derivative of a Gaussian (DOG) function:

$$\Psi_0(t) = \frac{(-1)^{m+1}}{\sqrt{\Gamma\left(m + \frac{1}{2}\right)}} \frac{d^m}{dt^m}\left(e^{-t^2/2}\right)$$

where t is time, m is the order (1, 2, etc), $$\frac{d^m}{dt^m}$$

is the derivative ($1^{st}$, $2^{nd}$, etc), and $\Gamma$ is the gamma function, which is factorial for complex numbers:

$$\Gamma(x) = \int_0^\infty t^{x-1} e^{-t} dt$$

where x is a non-integer or complex number, and t is time.

Other useful wavelets may include, for example, a Man wavelet, or Mexican hat; a Paul wavelet; a Daubechies wavelet; a Mathieu wavelet; a Legendre wavelet; a Beta wavelet; a Hermetian wavelet; a Shannon wavelet; or the like.

In some embodiments, by using interface module 32, a user may select the desired wavelet for analysis module 35 to apply to the amplification data. In other embodiments, the analysis module 35 may apply a plurality of wavelets to the amplification data and display the results of each wavelet to the user using interface module 32, or may automatically select a "better" result to display to the user. For example, the "better" result may include a greater maximum wavelet transformation magnitude, a lack of edge effects or other undesirable artifacts, or may satisfy some other criteria. In other embodiments, analysis module 35, or a user, may determine an approximate shape of the amplification data and select a wavelet whose shape is sufficiently similar to the shape of the amplification data. In other embodiments, the analysis module 35 can only select from a single wavelet to apply to the amplification data.

Wavelet transformation includes multiplying a time-varying signal (i.e., the amplification data or amplification curve), by the selected wavelet and integrating over all time:

$$W(a, b) = \frac{1}{\sqrt{a}} \int s(t) \Psi\left(\frac{t-b}{a}\right) dt$$

where s(t) is the time varying signal, $\Psi$ is the wavelet, a is the dilation, b is the time translation, and W is the magnitude of the wavelet transform at point (a,b). The time translation parameter, b, shifts the wavelet along the signal, effectively shifting the window over which the signal is inspected. The dilation parameter, a, is equivalent to an inverse frequency. Thus, a large value of the dilation parameter corresponds to inspecting the signal for low frequency components and a small value of the dilation parameter corresponds to inspecting the signal for high frequency components.

Analysis module 35 sets the dilation parameter, a, (104) and the time translation, b, (106) at an initial value, multiplies the wavelet function evaluated at (a, b) with the amplification data, and integrates the resulting function over all time, or cycles (108), to calculate the wavelet transformation magnitude at this time translation-dilation pair. The analysis module 35 may save the time translation, dilation, and calculated wavelet transformation magnitude in database module 33. The analysis module 35 then determines if a maximum value of the time translation parameter has been reached (110). If the analysis module 35 determines that the maximum value of the time translation parameter has not been reached, the analysis module 35 returns to step (106), increments the time translation parameter, multiplies the wavelet function evaluated at (a, b) with the amplification data, and integrates the resulting function over all time, or cycles (108). The analysis module 35 repeats this procedure until it determines that a maximum value of the time translation parameter has been reached for the value of the dilation parameter.

Time translation in the transformed function may be analogous to PCR cycle number in the original amplification data. While the magnitude of the time translation increment may be any desired value, in some embodiments, the increment may be set to one PCR cycle. In other embodiments, the time translation increment may be set to a fraction of a PCR cycle or multiple PCR cycles.

When analysis module 35 determines that a maximum value of the time translation parameter has been reached for the current value of the dilation parameter, analysis module determines if a maximum value for the dilation parameter has been reached (112). When analysis module 35 determines that the maximum value of the dilation parameter has not been reached, analysis module 35 returns to step (104) and increments the dilation parameter. The analysis module sets the time translation parameter (106), multiplies the wavelet function evaluated at the current time translation parameter and dilation parameter with the amplification data, integrates the function over all time (108), and increments the time translation parameter until the maximum time translation value is reached. Analysis module 35 repeats this cycle for each value of the dilation parameter until module 35 determines that a maximum value for the dilation parameter has been reached at step (112).

Data analysis module 35 or control module 31 may prepare the wavelet transformation data for output using interface module 32 in a variety of formats. For example, the transformed data may be represented as a two dimensional image. For example, in FIG. 11, a first axis (e.g., the x-axis) is time translation (or cycle), a second axis (e.g., the y-axis) is dilation, and a color, shade or intensity of each location (e.g., x-y coordinate) in the image corresponds to a magnitude of the wavelet at that time translation and dilation coordinate. As another example, the transformed data may be represented as a three-dimensional image, where a first axis is time translation, a second axis is dilation, and a third axis is a magnitude of the wavelet at the time translation and dilation coordinate. The transformed data may also be represented in table form, where, for example, the columns correspond to time translation, the rows correspond to dilation, and the entries in the table are the wavelet transformation magnitude at the corresponding time translation and dilation.

Next, analysis module 35 selects the frequency slice used to determine the $T_{max}$ value (114). As described briefly above, the dilation corresponds to an inverse frequency. Thus, when considering a wavelet transformation image, such as the image shown in FIG. 11, a set of wavelet transformation magnitudes corresponding to all time translation values at a single dilation value, shown as line 111, may be referred to as a frequency slice. In some embodiments, the analysis module 35 may select a predetermined frequency slice with which to determine the $T_{max}$ value. In other embodiments, a user may input into interface module 32 which frequency slice analysis module 35 is to use. In yet other embodiments, analysis module 35 may select a plurality of frequency slices and average the $T_{max}$ values of each frequency slice to determine an average $T_{max}$ for the amplification data.

Once the analysis module 35 or a user selects the frequency slice(s) that module 35 is to use to determine the $T_{max}$ value, the analysis module proceeds to determine the $T_{max}$ value (116). Analysis module 35 may determine the cycle or fraction of a cycle at which a local maximum wavelet transformation magnitude occurs for the selected frequency slice(s). Module 35 may determine this graphically, from inspection of a data set including the wavelet transformation magnitudes for the selected frequency slice, by a linear regression fit of a parabolic or other shaped curve to the wavelet transformation data proximate the local maximum wavelet transformation magnitude, or a combination of graphical and inspection techniques, for example.

Figure 12:
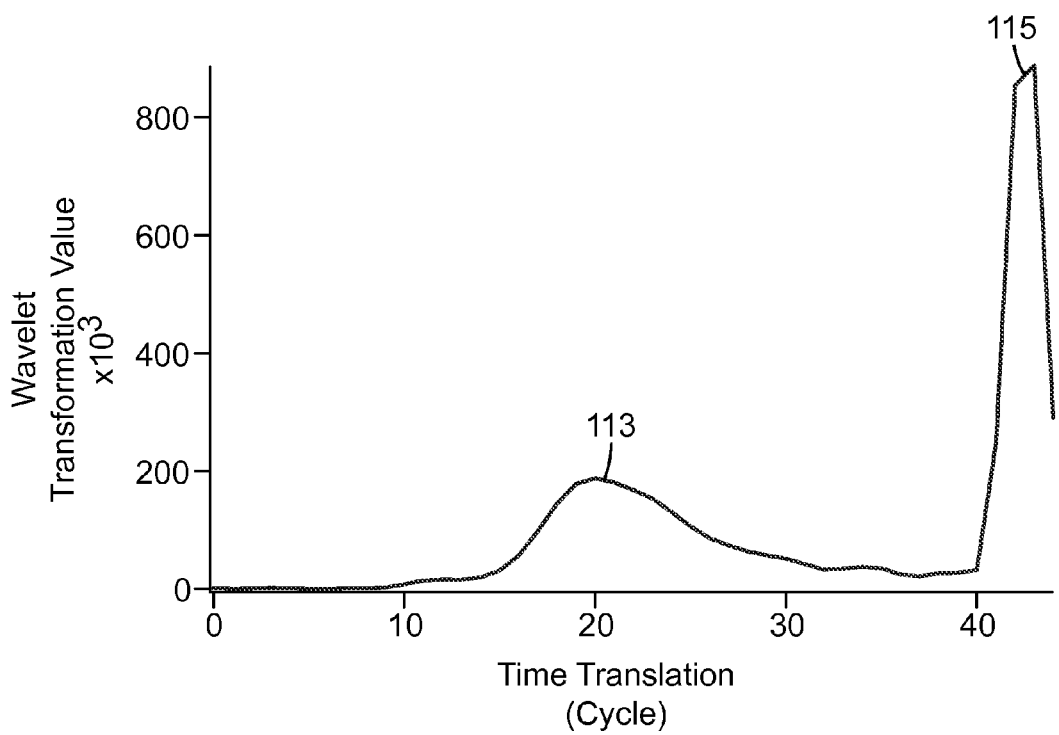
FIG. 12 is a plot of wavelet transformation value versus time translation for the frequency slice of FIG. 10.

FIG. 12 illustrates a line graph of the wavelet transformation magnitude as a function of time translation (or cycle) for the frequency slice represented by line 111. The line graph includes two peaks, local maximum 113, located at approximately cycle 20, and global maximum 115, located at approximately cycle 40. In some embodiments, analysis module 35 may select the cycle at which the global maximum wavelet transformation magnitude occurs as the $T_{max}$ value. However, in some embodiments, this may lead to inaccuracies. For example, in the illustrated embodiment, the global maximum 115 is a result of an edge effect from having a limited number of dilation values. In other embodiments, inaccuracies may occur due to other artifacts, which may be filtered out using appropriate techniques. In the embodiment of FIG. 12, analysis module 35 determines global maximum 115 to be an edge effect and selects the local maximum 113 as the peak of interest. Thus, the analysis module 35 determines the $T_{max}$ to be approximately 20, corresponding to the cycle at which the local maximum 113 occurs. Once the $T_{max}$ value is determined, interface module 32 may display the $T_{max}$ value graphically, as text, or in another suitable form, including any format described above with respect to FIGS. 1 and 4-7.

Figure 13:
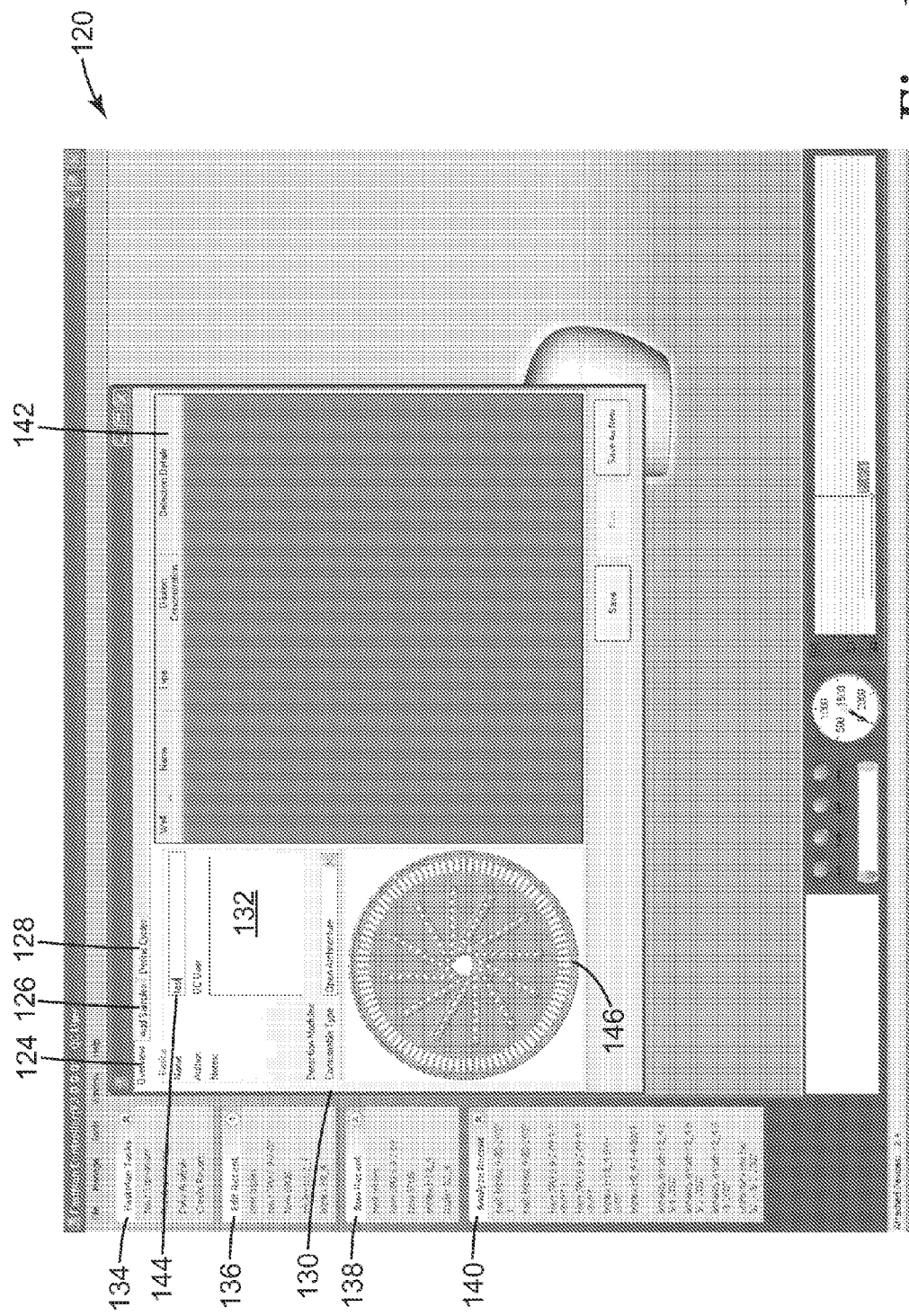
FIGS. 13-22 are example user interface screens presented to a user by a data analysis device.

FIGS. 13-22 show exemplary user interface screens that interface module 32 may present to a user. FIG. 13 illustrates a screen 120 including a window 122 for entering parameters for the PCR reaction. The window 122 includes an "Overview" tab 124, an "Add Samples" tab 126 and a "Define Cycles" tab 128 which are linked to separate view panes within window 122. The "Overview" tab 124 is selected in screen 120. The view pane 142 linked to the "Overview" tab 124 includes a text box 132, which accepts textual entry of notes about the PCR reaction to be run, a drop-down list 130 that allows a user to enter the type of disk 13 being used, and a text box 144, which allows a user to enter a name of the test. The view pane 142 may also include a graphical display 146 of the disk 13 selected using drop-down list 130. While FIG. 13 illustrates the type of disk 13 as being selected using a drop-down list 130, in other embodiments, the type of disk 13 may be selected by another user interface element, such as, for example, a radio button, an icon, a text-box, a check box or the like.

Screen 120 also includes a plurality of navigation widgets 134, 136, 138 and 140, each including a number of hyperlinks. Tasks widget 134 includes hyperlinks that direct a user to screens for performing common tasks, such as defining a new experiment, running an experiment, analyzing data, or creating a report. Edit widget 136 includes hyperlinks that direct a user to an editing screen that allows editing of a recently defined PCR reaction parameter set. Widget 138 includes hyperlinks that direct a user to a screen that allows a user to run the currently loaded disk 13 with a recently defined PCR reaction parameter set. Widget 140 includes hyperlinks that direct a user to a screen that allows a user to analyze recently collected and saved PCR amplification data.

Figure 14:
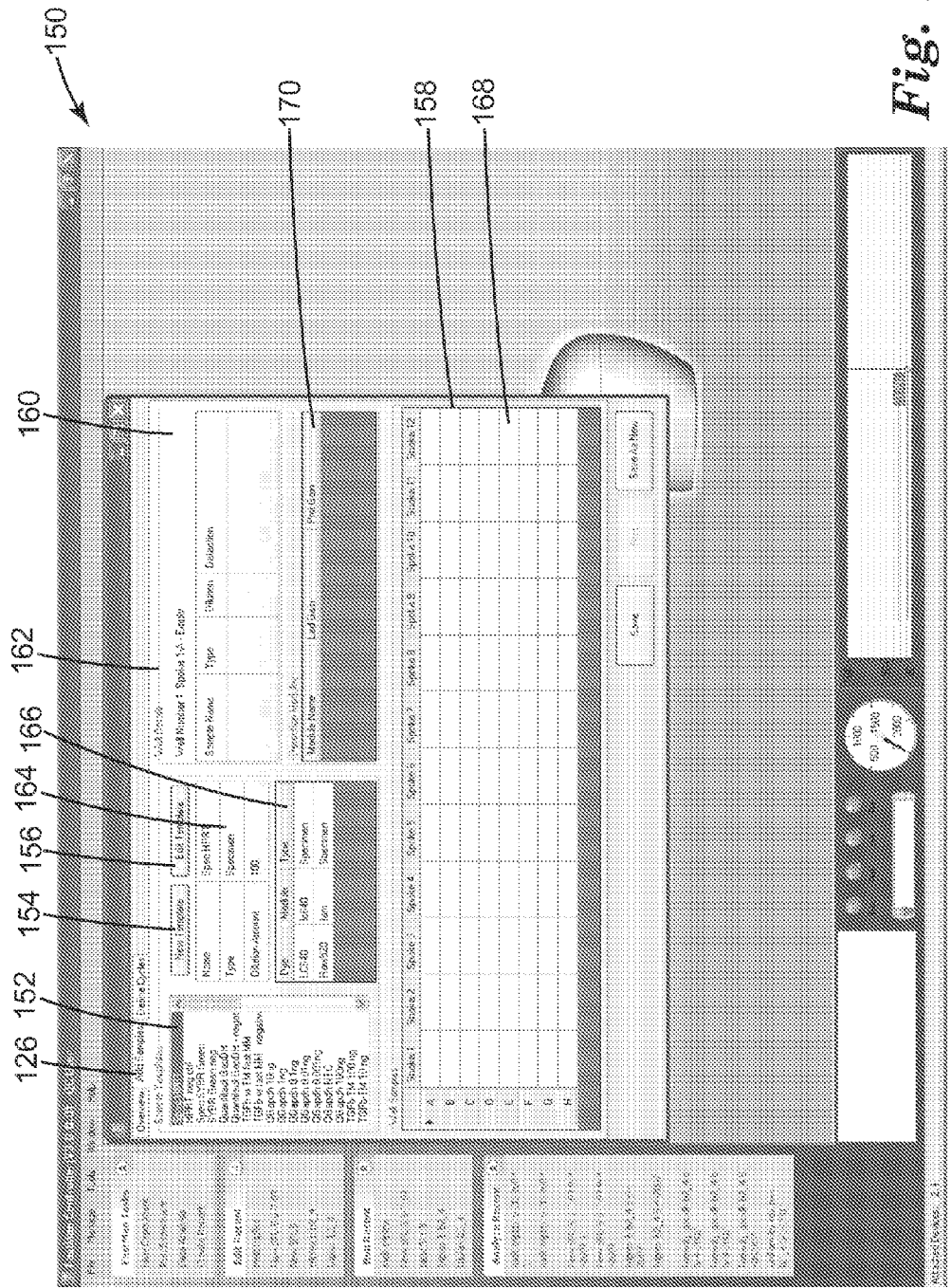

FIG. 14 shows a screen 150 in which the "Add Samples" tab 152 of window 122 is selected. The "Add Samples" tab 152 presents a view pane 162 that allows a user to enter parameters about the samples 17 contained in disk 13. View pane 162 includes a list 152 that allows a user to select from a plurality of sample templates that include predefined parameters, such as composition and amount. View pane 162 also includes a new template button 154, which allows a user to create a new template and enter amount and composition information about that template, and an edit template button 155, which may allow a user to edit an existing template, such as one of the templates listed in list 152. View pane 162 may further include sample template data grid 164 and sample dye data grid 166, which present parameters of the selected sample template, such as the sample type, the dilution amount, and the dye and corresponding detector module to be used. In some embodiments, data grids 164 and 166 may also allow editing of displayed parameters.

View pane 162 may also include a well sample data grid 158 that presents sample information for each of the chambers on disk 13 in a corresponding cell 168. In the illustrated embodiment, the disk 13 includes 12 spokes and each spoke includes eight chambers (A-H), for a total of 96 samples. An exemplary disk 13 of this type is shown in graphical display 146 of screen 120. Well sample data grid 158 may also allow entry of the sample template name in each cell 168 of the grid 158. However, in some embodiments, grid 158 may only display the sample template name for each sample chamber in the corresponding cell 168.

In some embodiments, data grid 158 may display a limited amount of detail about each sample 17, such as the sample template name. Further details regarding the sample 17 in the selected cell 168 of data grid 158 may be displayed in well detail data grid 160. These details may include a sample name, sample type, sample dilution, and detection type.

View pane 162 also includes a detection module data grid 170, which may display parameters of the detection module, including, for example, detection module name, the LED gain and the photomultiplier tube gain. In some embodiments, detection module data grid 170 may allow editing of the detection module parameters, while in other embodiments, the grid 170 may simply display the parameters.

Figure 15:
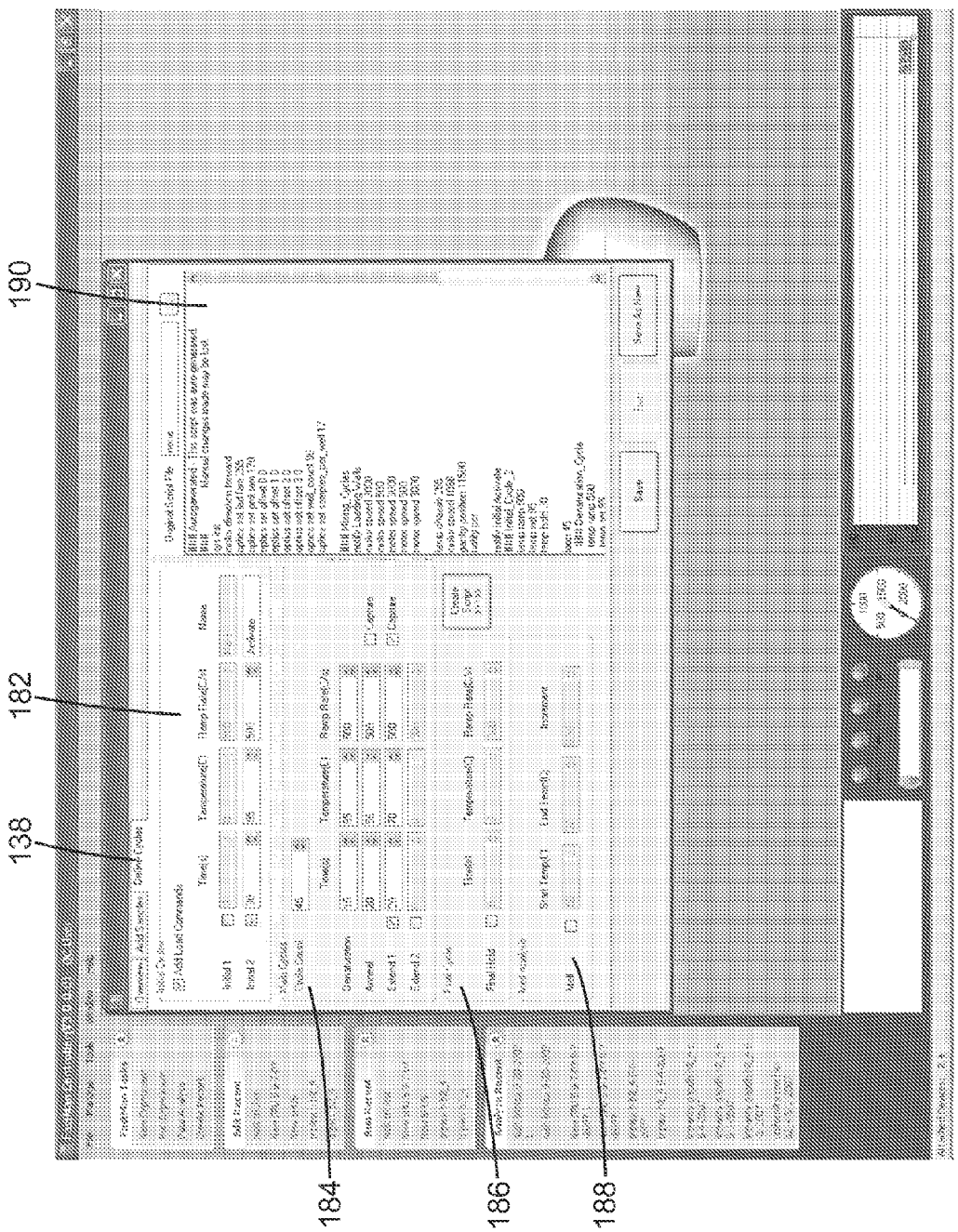

FIG. 15 illustrates a user interface screen 180 including window 122 in which "Define Cycles" tab 138 is selected. When "Define Cycles" tab 138 is selected, window 122 displays view pane 192, which allows a user to set PCR cycle parameters. View pane 192 includes a plurality of user interface elements, which allow a user to define the parameters of the PCR cycles performed during the PCR analysis session. For example, view pane 192 includes an Initial Cycles section 182, which comprises elements such as check boxes, drop-down lists, text-boxes, and the like for activating at least one initial PCR cycle and setting the parameters of this at least one initial PCR cycle. Parameters of the at least one initial PCR cycle may include a length of time, a desired temperature, a temperature ramp rate up to the desired temperature, and a name for each of the at least one initial cycle. The initial cycle may assist in preparing the sample(s) for undergoing the main PCR cycles, but may not be used in some embodiments.

View pane 192 may also include a Main Cycles section 184, which includes a plurality of user interface elements that allow a user to set parameters of the main PCR cycles. Main Cycles section 184 may include, for example, radio buttons, drop-down menus, check-boxes, text boxes or the like. The Main Cycles section 184 may allow a user to set the number of cycles and the time, temperature and temperature ramp rate for each of the denaturation, annealing, and extension steps. In addition, the Main Cycles section 184 may allow a user to specify multiple extension steps, such as, for example, two extension steps. Main Cycles section 184 may also allow a user to select at what point during the main cycle data optical module 16 and detector 18 capture fluorescence data from the sample(s).

View pane 192 may further include a Final Cycle section 186 and a Melt Analysis section 188, which allow a user to activate and edit these optional cycles. The Final Cycle section 186 and Melt Analysis section 188 each include user interface elements such as, for example, check-boxes, icons, drop-down lists, radio buttons, and the like for activating the respective cycles and entering or selecting values for the parameters of each cycle. For example, the selectable parameters for the final cycle may include time, temperature and ramp rate. The selectable parameters for the melt analysis may include a start temperature, an end temperature, and a temperature increment.

In the embodiment illustrated in FIG. 15, view pane 192 also includes a scripting text box 190, which allows a user to specify the parameters of a PCR analysis session through text entry. Scripting text box 190 may allow a user to view, input or edit parameters of the PCR analysis session in further detail than that available to the user through use of the Initial Cycle section 182, Main Cycle section 184, Final Cycle section 186 and Melt Analysis section 188.

Figure 16:
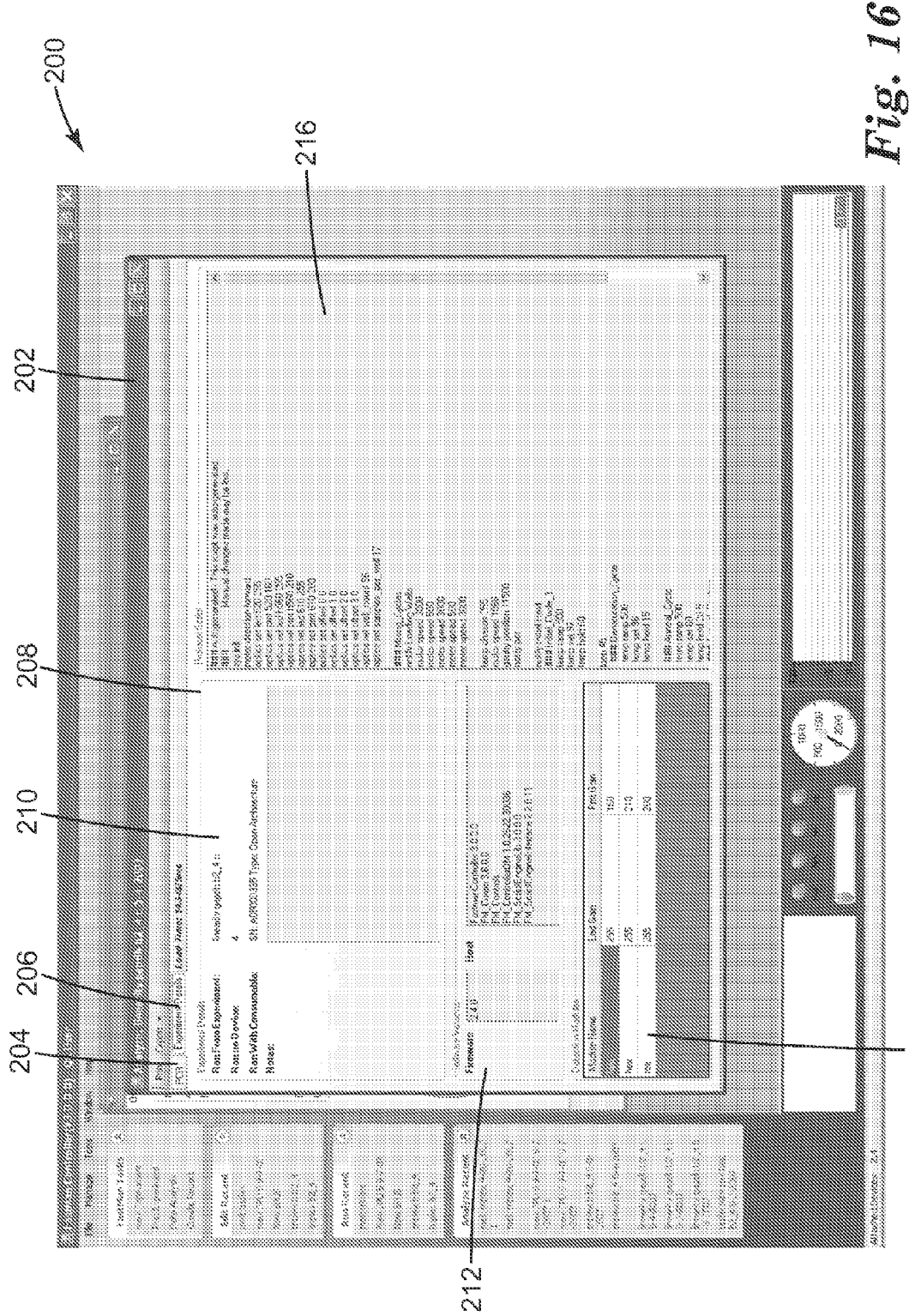

FIG. 16 illustrates an exemplary user interface screen 200 including an analyze window 202. The analyze window includes a PCR tab 204 and an Experiment Details tab 206, which is selected in FIG. 16. The Experiment Details tab 206 displays a view pane 208 that includes an experiment details section 210, a software versions section 212, a detection modules section 214 and a script section 216. Experiment details section 210 displays details about the PCR analysis session, such as, for example, the name of the PCR analysis session, the device 12 on which the PCR analysis session was run, the type of disk 13 used, and any notes entered by a user at the time of the analysis session. The software versions section 212 may display version information about software and firmware used by fluorescence detection device 12 and data analysis device 11. Detection modules section 214 may display a name of any optical module 16 used in the PCR analysis session, an LED gain of the module 16, and the photomultiplier tube gain of the module 16. Script section 216 may display the script control module 31 used to control detection device 12 during the PCR analysis session.

Figure 17:
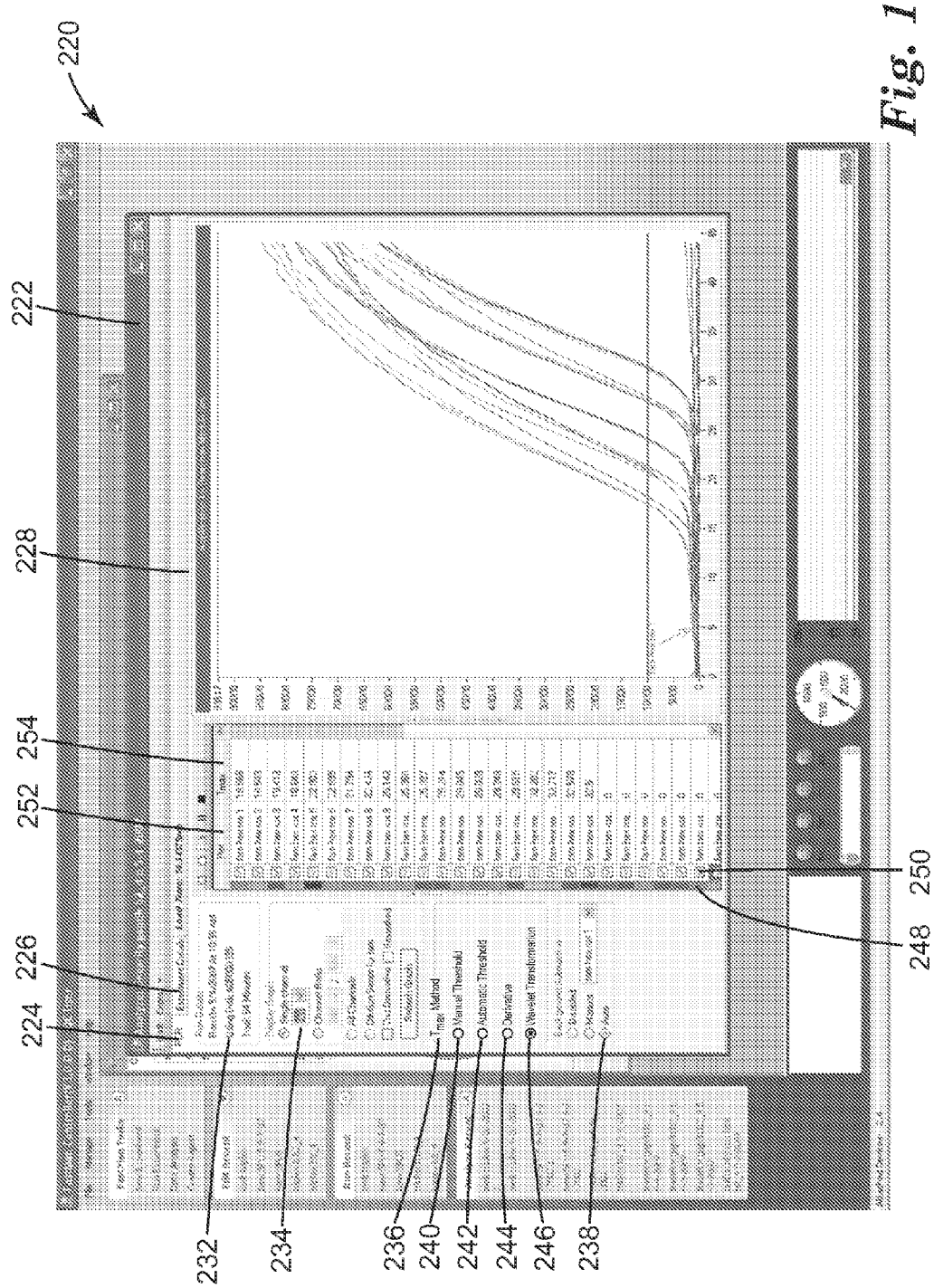

FIGS. 17-21 illustrate example user interface screens 220, 260, 270, 280 and 290 displaying PCR amplification curves for different sample types. FIG. 17 illustrates an example user interface screen 220 including a window 222 (similar to window 202 of FIG. 16) with a PCR tab 224 and an Experimental Details tab 226. The Experimental Details tab 226 may lead to a view pane similar to view pane 208 of FIG. 16. In the embodiment shown in FIG. 17, the PCR tab 224 is selected and a view pane 228 including a graph 230 of PCR amplification curves is displayed. The PCR amplification curves in FIG. 17 were generated by performing PCR on FAM-labeled GAPDH (glyceraldehyde 3-phosphate dehydrogenase) gene expression samples. The view pane 228 also includes a Run Details section 232, a Display Graph section 234, a $T_{max}$ Method section 236 and a Background Subtraction section 238, which allow a user to modify what information graph 230 displays and how the $T_{max}$ or $c_t$ values for each curve are calculated.

For example, Display Graph section 234 includes a plurality of user interface elements that allow a user to select the information displayed on graph 230. In the illustrated embodiment, the user interface elements in Display Graph section 234 include radio buttons that allow selection of the type of graph, a drop-down list for selecting the channel displayed in a single channel graph, check boxes for selecting any preprocessing applied to the data before display, and a button for refreshing the graph when changes are made. In other embodiments, the user interface elements may include other elements, and may allow a user to select other types of graphs or other preprocessing options. Graph 230 of FIG. 17 is set to display a single channel line graph of amplification data from a "fam" optical module 16, as indicated in Display Graph section 234.

The $T_{max}$ Method section 236 may allow a user to select the type of analysis applied to the amplification data to determine a $T_{max}$ value or $c_t$ value. In some embodiments, the $T_{max}$ Method section 236 may allow a user to select from a plurality of analysis methods, such as manual threshold, automatic threshold, derivative, Fourier transform, wavelet analysis, or the like. In other embodiments, the $T_{max}$ Method section 236 may allow the user to select from a plurality of wavelets for application in the wavelet transformation method. In other embodiments, the view pane 228 may not include a $T_{max}$ Method section 236. Instead, wavelet transformation may be the only method used to determine the $T_{max}$, and the wavelet used in the wavelet transformation method may be automatically determined by control module 31, or may be limited to a single wavelet.

In the illustrated embodiment, a user may select between multiple methods of determining $T_{max}$. Further, in some embodiments, the user may select settings for at least some of the methods, such as the threshold for the manual threshold method, the minimum amplification for the derivative method, and the parameters by which the automatic threshold is determined. Additionally, while not shown in FIG. 17, in some embodiments the user may select the wavelet which analysis module 35 uses in the wavelet transformation. Different wavelets may be more or less suitable for different amplification data. For example, a wavelet that matches the shape of the amplification data more closely may be preferred in some embodiments. In other embodiments, it may be preferable to use a single wavelet in all analyses to facilitate comparison of the results across multiple analyses, for the analysis module 35 to automatically select the wavelet, or for the analysis module 35 to apply a plurality of wavelets to the amplification data and present the user with only the "best" results.

Further, in some embodiments, as described above, the interface module 32 may present a user with a table, graph, or image of the wavelet transformation data. The user may then select the frequency slice or slices which analysis module 35 uses to determine the $T_{max}$ value.

View pane 228 also includes a Background Subtraction section 238 that include user interface elements that allow a user to select whether analysis module 35 subtracts off background noise from a signal before displaying it on graph 230. In the embodiment shown in FIG. 17, the Background Subtraction section 238 allows a user to select between disabling background subtraction, using a selected signal as the background, and automatic background subtraction, where analysis module 35 determines automatically how to subtract off background noise.

View pane 228 further includes a Sample data grid 248. The Sample data grid 248 includes a row for each sample, and displays the sample name 252 and calculated $T_{max}$ value 254. The sample data grid 248 also includes a check box 250 for each sample that allows a user to select whether the amplification curve for that sample is displayed on graph 230.

Figure 18:
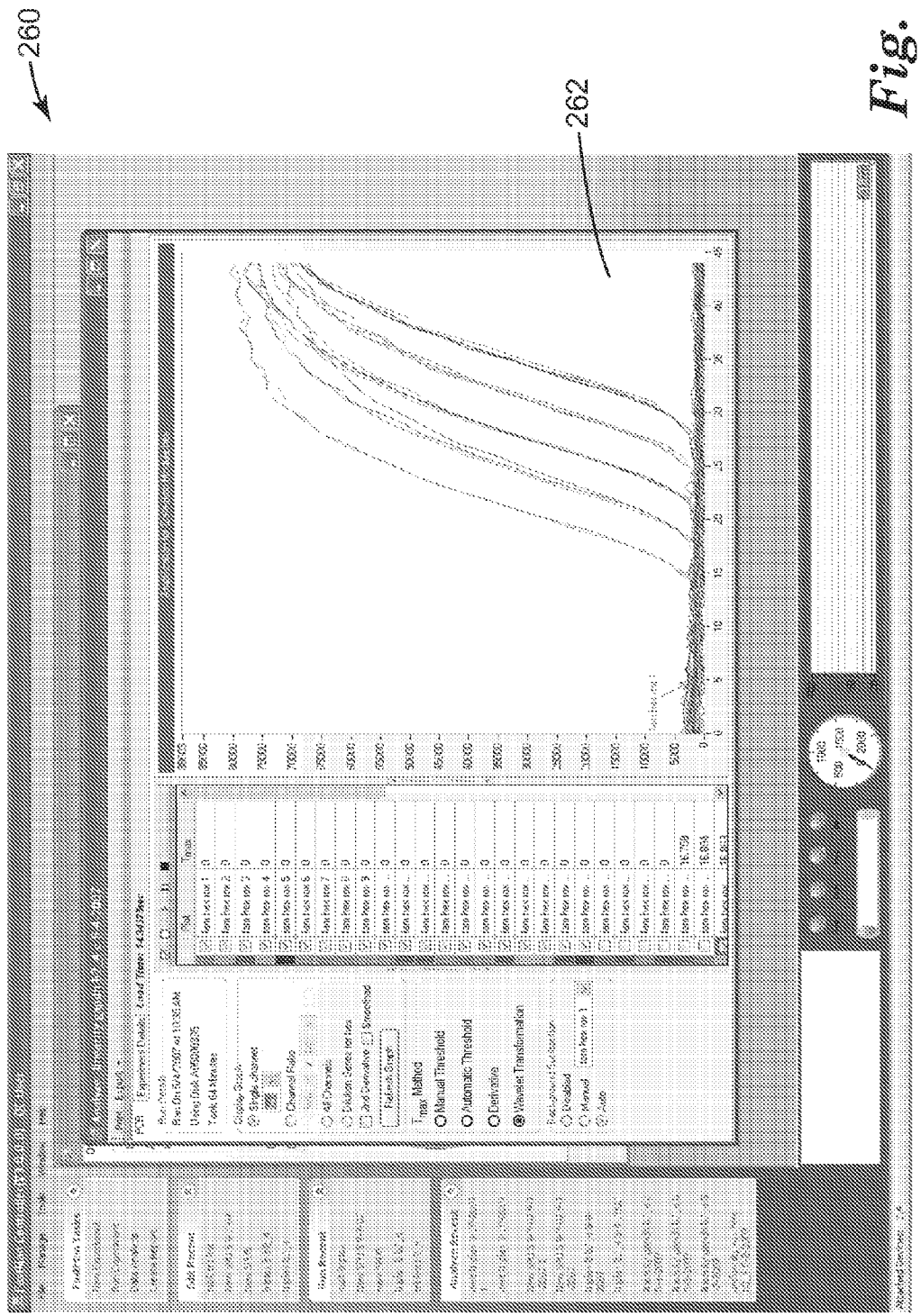

FIG. 18 illustrates an example user interface screen 260 similar to user interface screen 220 of FIG. 16, but screen 260 includes a graph 262 displaying PCR amplification curves of HEX-labeled GAPDH samples.

Figure 19:
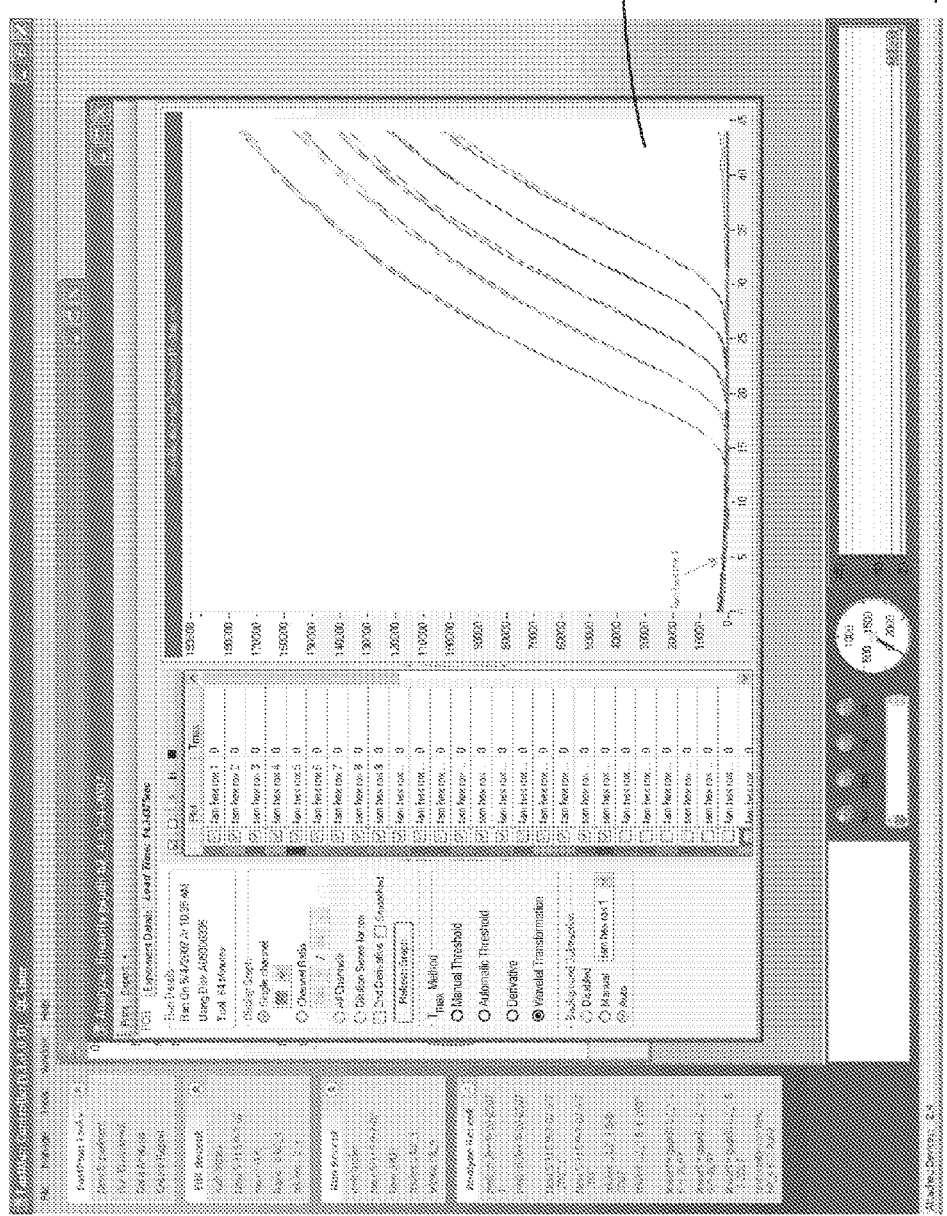
Figure 20:
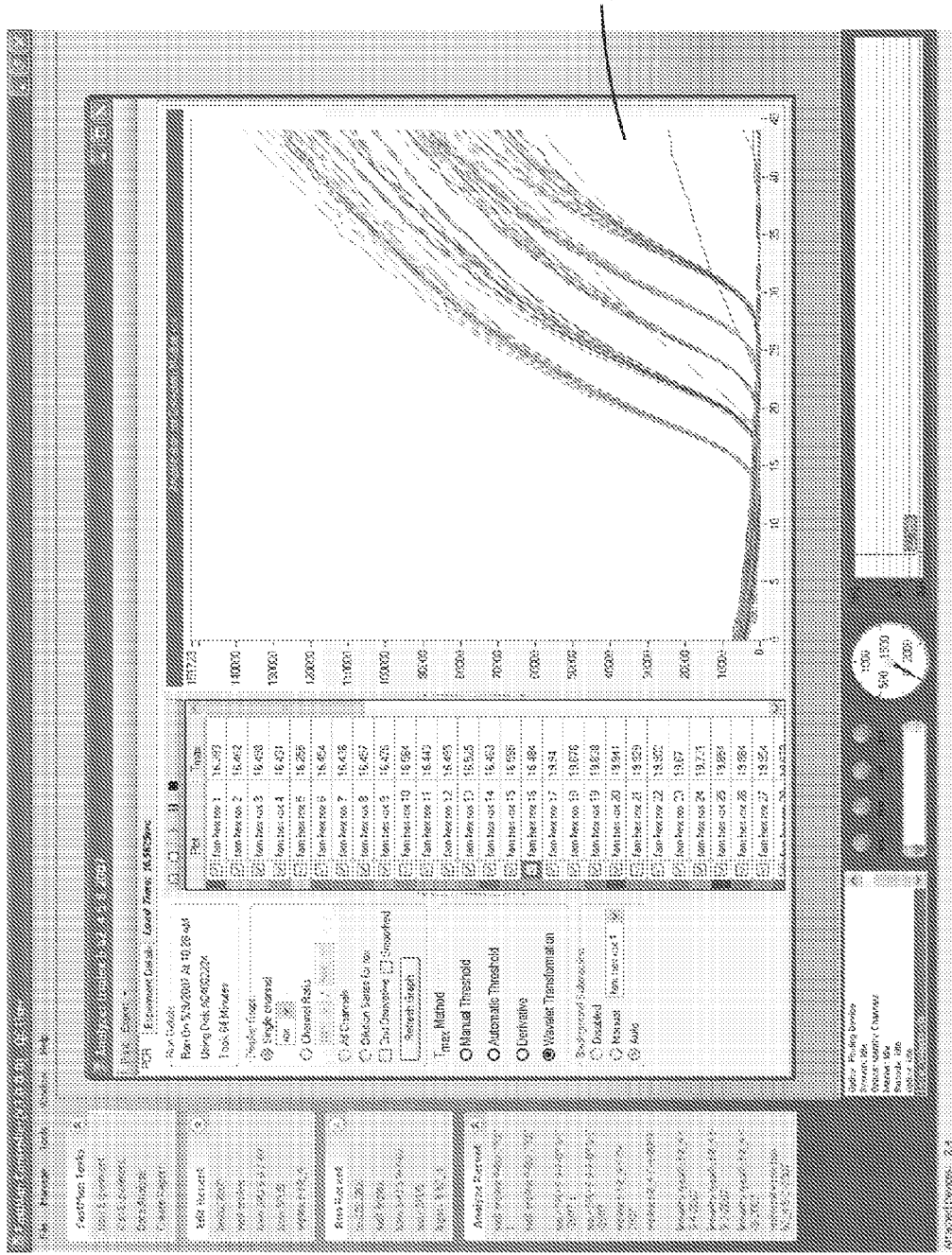

FIGS. 19 and 20 illustrate exemplary user interface screens 270 and 280 that are similar to user interface screen 220 of FIG. 17, but screens 270 and 280 includes a graphs 272 and 282, respectively, that display PCR amplification curves of ROX-labeled GAPDH.

Figure 21:
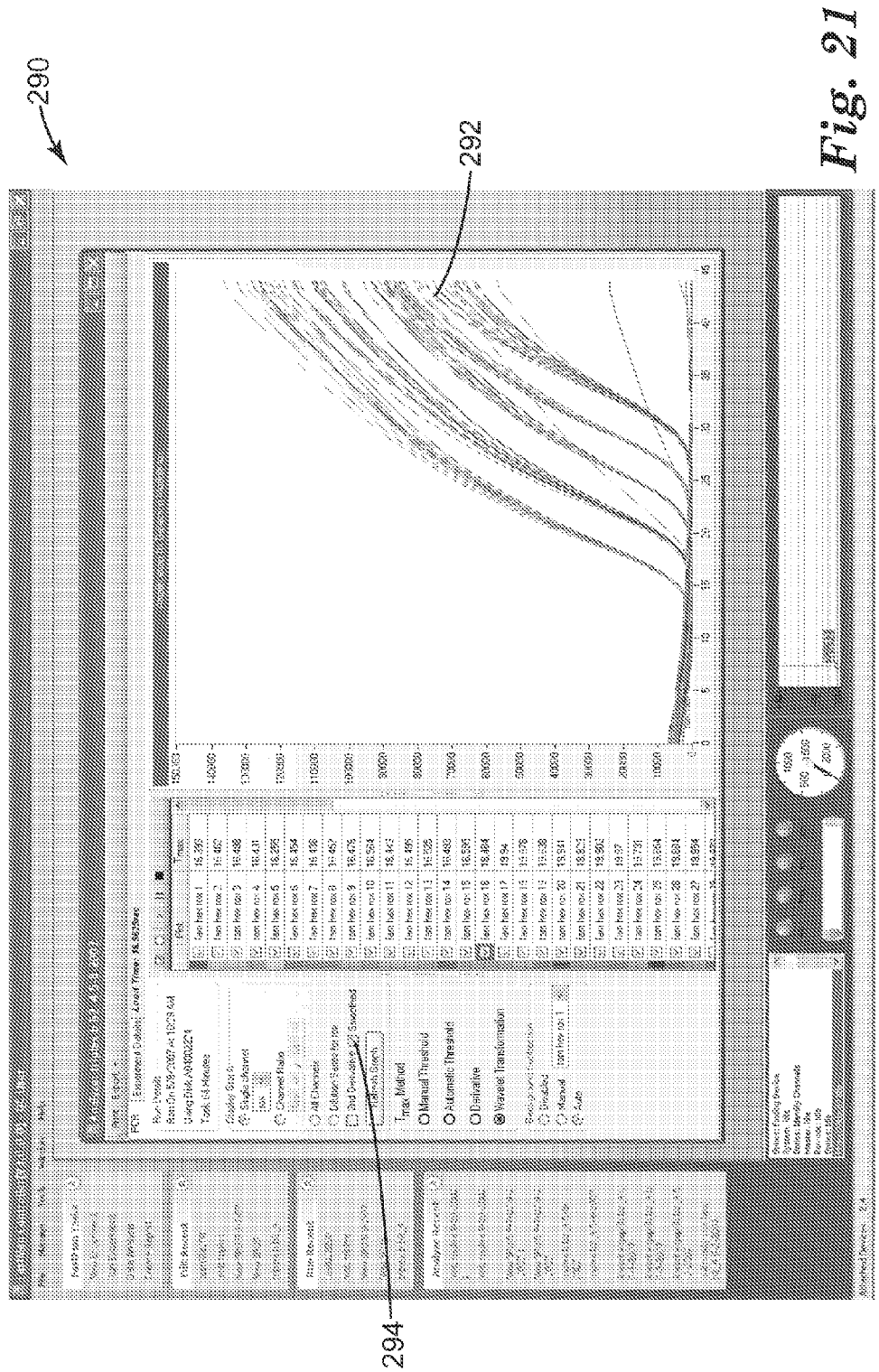

FIG. 21 illustrates an exemplary user interface screen 290 including a graph 292 of ROX-labeled GAPDH PCR amplification curves similar to those of FIG. 20. However, in FIG. 21, the amplification curves have been smoothed prior to being displayed, as indicated by check-box 294.

Figure 22:
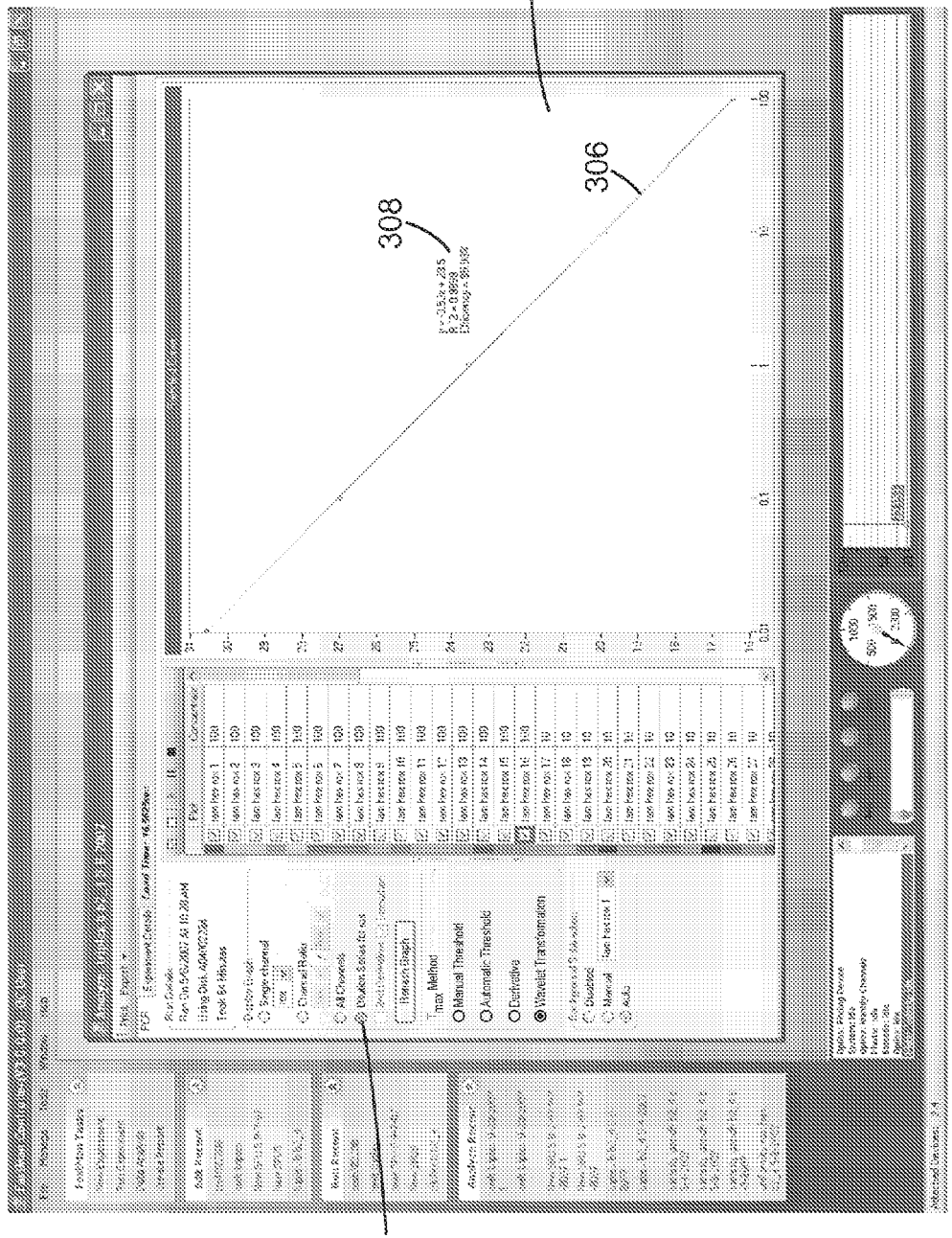

FIG. 22 illustrates a user interface screen 300 similar to user interface screens 240, 260, 270, 280 and 290 of FIGS. 17-21. However, in screen 300 of FIG. 22, radio button 302 corresponding to "Dilution Series for rox" is selected and a standard curve 306 based on this dilution series is displayed on graph 304. The standard curve is a graph of the $T_{max}$ value of a sample versus a logarithm of the initial concentration of the sample (or the initial concentration on a logarithmic scale). The standard curve is a straight line on this semi-logarithmic graph, with an equation of a simple line. The analysis module 35 may calculate the equation of the line, along with an $R^2$ value of the linear regression fit of this line to the actual $T_{max}$ data and an efficiency of the PCR reaction, and display this information 308 on the graph 304 or another section of window 300.

EXAMPLES

Figure 23:
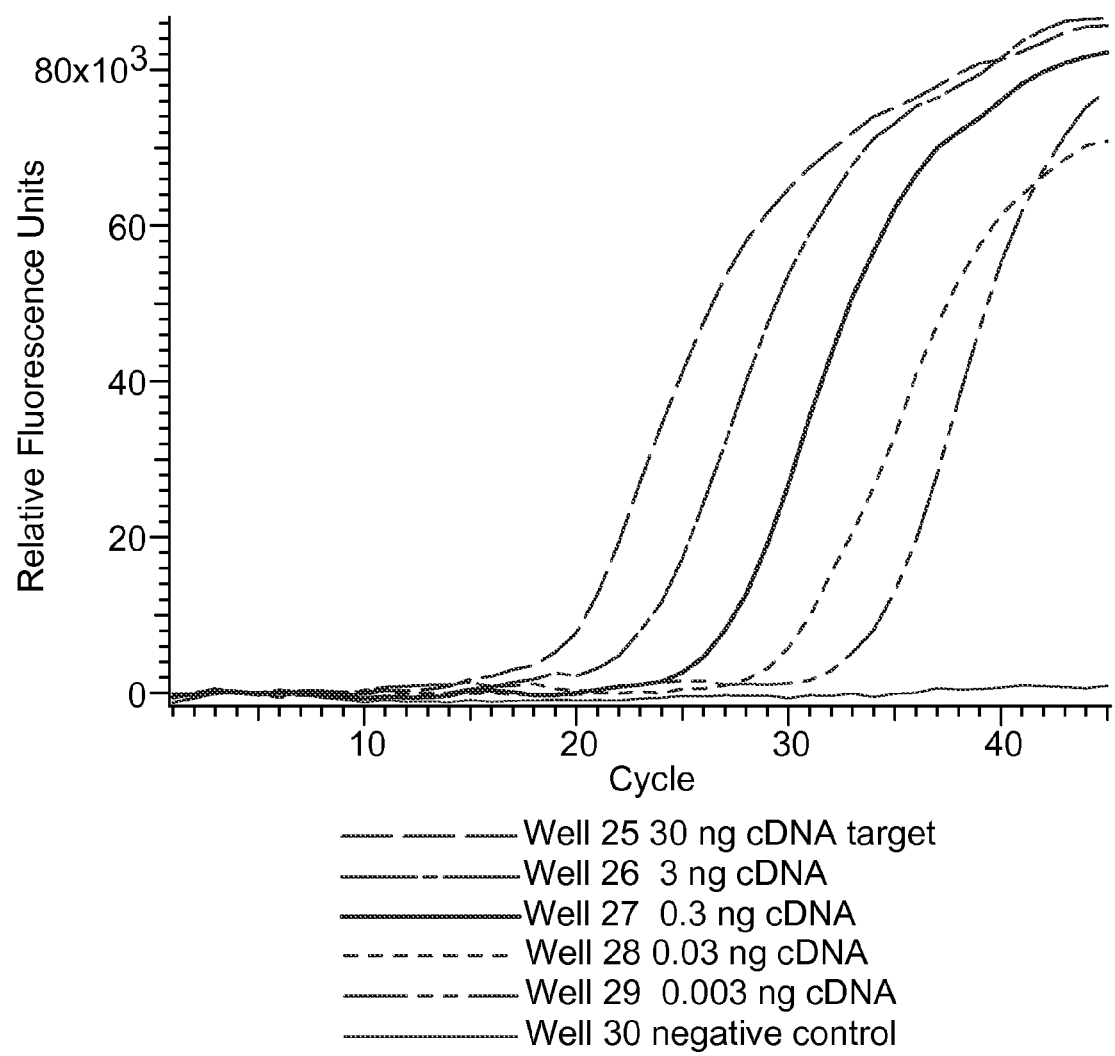
FIG. 23 is an example plot of fluorescence versus cycle number for a plurality of samples including different initial amounts of cDNA.

A series of real-time PCR reactions were performed using a GAPDH target primer and complimentary DNA (cDNA) standards. The real-time growth curves are shown in FIG. 23. For every template concentration decrease of ten, the growth is delayed, consistent with PCR theory.

Figure 11:
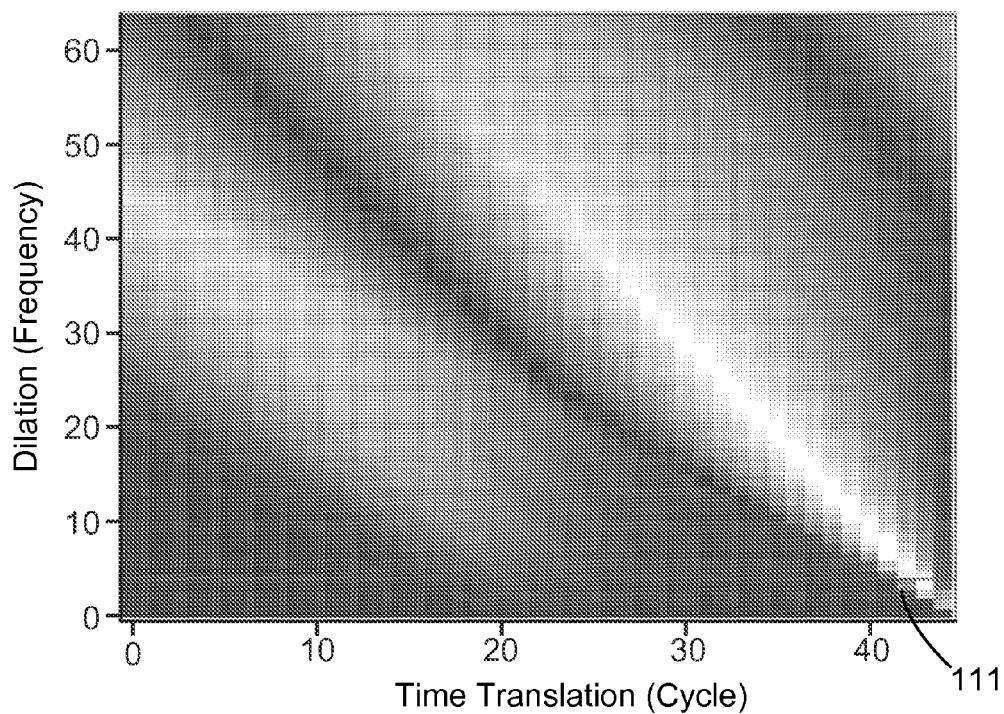
FIG. 11 is an example image of wavelet transformation data produced by applying wavelet transformation to nucleic acid amplification data.
Figure 24:
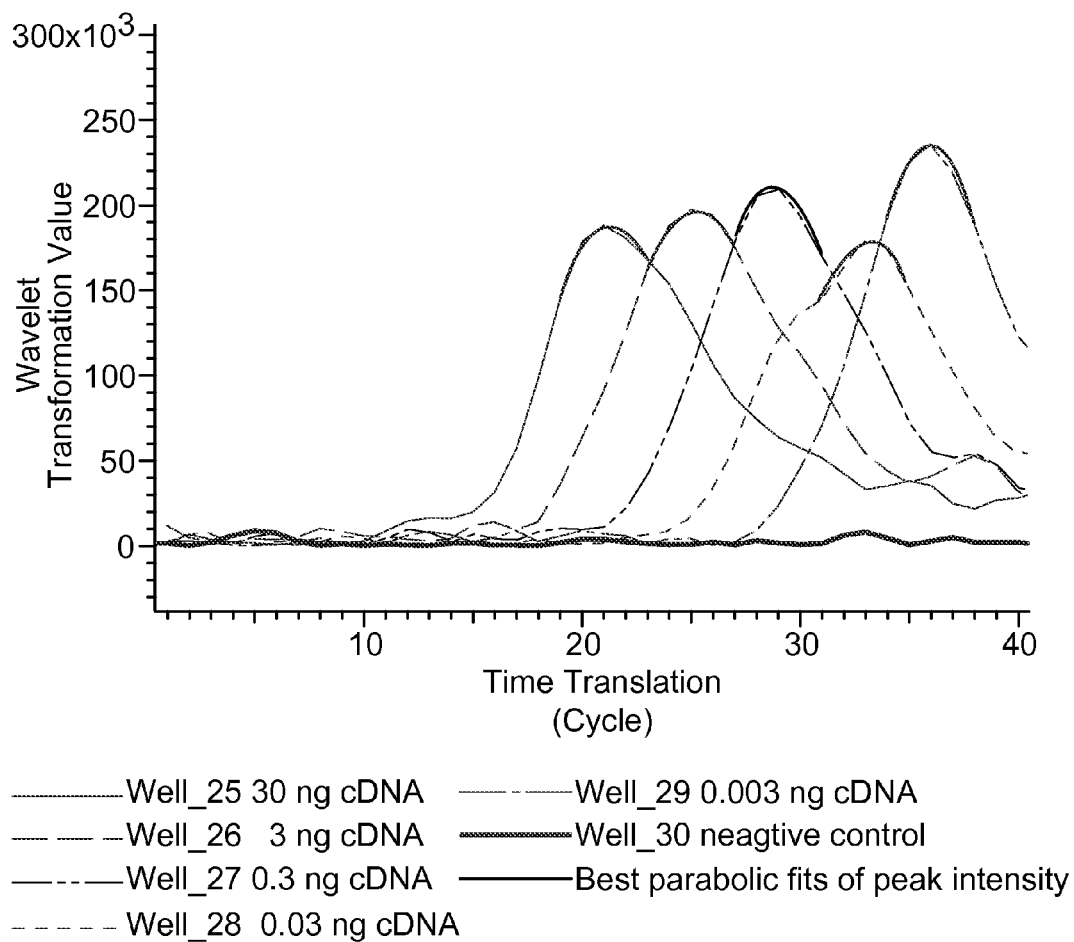
FIG. 24 illustrates a parabolic curve fit to a peak of a frequency slice of a wavelet transform using a Haar wavelet basis function for a plurality of cDNA samples.

For each amplification curve, a continuous wavelet transformation (CWT) was calculated using a set of 64 dilations using a Harr wavelet basis function. For each amplification curve, a two-dimensional image was obtained that was sliced at different frequencies to determine the $T_{max}$. FIG. 11 shows the CWT of the sample that contained 30 ng of cDNA template. Line 111 corresponds to the fourth frequency slice, which has an intensity profile as shown in FIG. 12. The spike 115 is the end is an edge effect from having a small number of dilation values. Neglecting the edge effect, there is a visible local maximum of the intensity profile 113 near cycle 20. The maximum of the intensity profile, $T_{max}$, was calculated for the fourth frequency slice for each of the samples. $T_{max}$ was determined by performing a least-squares parabolic fit over the maximum of the intensity profile and determining the maximum of the parabolic fit. FIG. 24 shows the intensity profiles of the fourth dilation for each sample in the dilution series and the parabolic fit over each of the peaks for determination of the $T_{max}$ values.

Figure 25:
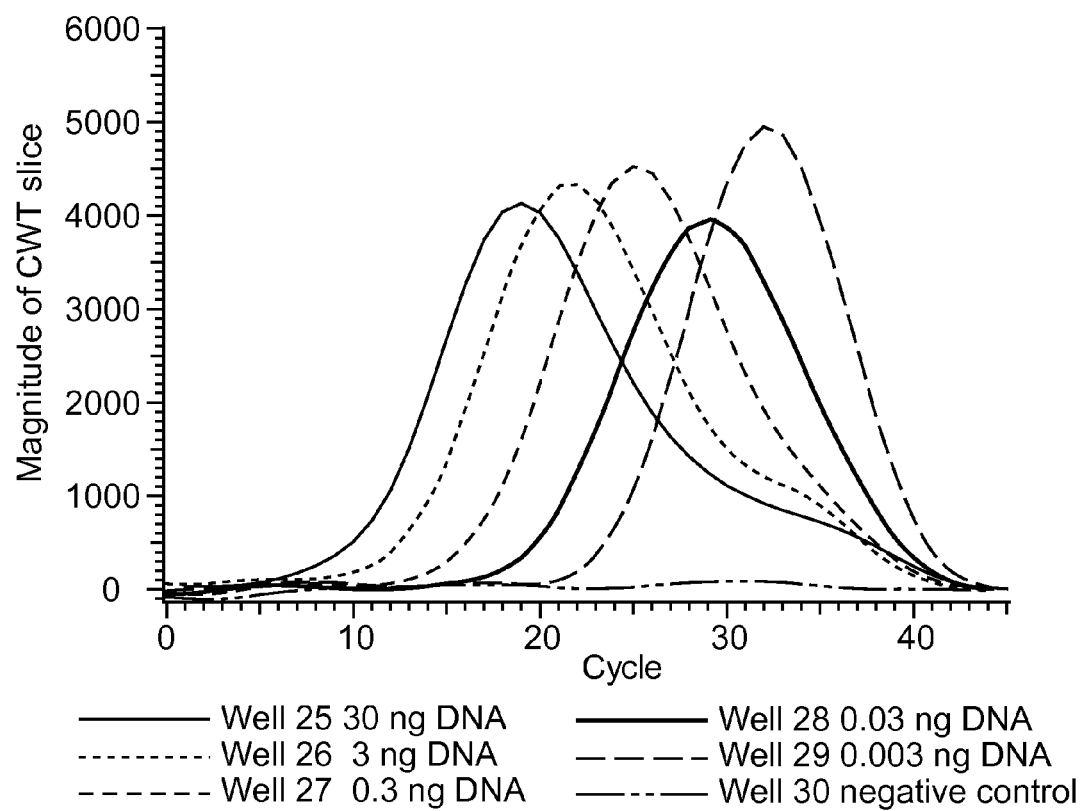
FIG. 25 illustrates a parabolic curve fit to a peak of a frequency slice of a wavelet transform using a derivative of a Gaussian function for a plurality of cDNA samples.

The amplification curves in FIG. 11 were also analyzed by a continuous transformation (CWT) with the use of the first derivative of a Gaussian (DOG) as a basis set and a total number of 512 dilations. FIG. 25 shows the magnitude of the $25^{th}$ frequency slice. Note that the use of a much larger set of dilations has resulted in the elimination of the edge effects that may occur with the analysis of the data using a Haar wavelet basis function. A $T_{max}$ value for the $25^{th}$ frequency slice was calculated by a least squares parabolic fit over the maximum of the intensity profile and determining the maximum of the fit. Table 1 compares the $T_{max}$ values of the DOG Wavelet Transform, the $T_{max}$ values of the Haar Wavelet Transform, and the Ct determined by the threshold and derivative techniques.

TABLE 1

Comparison of Wavelet Transformations with Other Techniques

| Well | cDNA Amount (ng) | Threshold $C_t$ | Derivative $C_t$ | Haar Wavelet Transformation $T_{max}$ | DOG Wavelet Transformation $T_{max}$ |
|---|---|---|---|---|---|
| 25 | 30 | 20.607 | 19.969 | 21.31 | 19.09 |
| 26 | 3 | 23.085 | 23.338 | 25.24 | 22.71 |
| 27 | 0.3 | 27.34 | 27.239 | 28.81 | 26.21 |
| 28 | 0.03 | 30.973 | 29.957 | 33.27 | 30.09 |
| 29 | 0.003 | 34.286 | 34.51 | 35.82 | 33.17 |
| 30 | 0 (control) | — | — | — | — |
| Slope | | −3.52 | −3.56 | −3.7 | −3.55 |
| PCR Efficiency | | 96.10% | 95.40% | 93.10% | 95.58% |
| $R^2$ Value | | 0.995 | 0.9954 | 0.994 | 0.999 |

The PCR efficiency was determined by calculating the slope of a linear least squares fit of the cycle (either $C_t$ to $T_{max}$)

versus the logarithm of the cDNA template amount. The slope of the fit is related to PCR efficiency by:

$$\text{Efficiency} = \frac{(10^{-1/slope})}{2} \times 100\%$$

As shown in Table 1, the use of different wavelet transforms may vary the $T_{max}$ value. However, the correlation between $T_{max}$ and Ct of a given method, such as the threshold and derivative techniques, remain substantially equivalent.

Various embodiments of the invention have been described. These and other embodiments are within the scope of the following claims.

The invention claimed is:

1. A method comprising:
performing a PCR analysis of a nucleic acid sample, wherein the PCR analysis comprises a plurality of PCR cycles;
from the PCR analysis, acquiring amplification data proportional to an amount of nucleic acid present for each of the plurality of PCR cycles;
applying wavelet transformation to the amplification data to determine a PCR cycle corresponding to a point within a growth period of the amplification data; and
updating a display based on the PCR cycle corresponding to a point within a growth period of the amplification data.

2. The method of claim 1, wherein applying wavelet transformation comprises:
generating an amplification curve from the amplification data, the amplification curve representing growth of the nucleic acid sample versus PCR cycle; and
applying continuous wavelet transformation (CWT) to the amplification curve to decompose the amplification curve into frequency components while maintaining PCR cycle localization for the frequency components along the amplification curve.

3. The method of claim 1,
wherein the amplification data represents growth of the nucleic acid sample over time, and
wherein applying wavelet transformation comprises applying discrete wavelet transformation (DWT) to the amplification data to decompose the amplification data into frequency components while maintaining PCR cycle localization for the frequency components with respect to time.

4. The method of claim 1, wherein the PCR cycle corresponding to a point within a growth period of the amplification data comprises a fraction of a PCR cycle.

5. The method of claim 1, wherein the PCR cycle corresponding to a point within a growth period of the amplification data is referred to as a $T_{max}$ value.

6. The method of claim 1, wherein the PCR cycle corresponding to a point within a growth period of the amplification data corresponds to an approximate onset of the growth period.

7. The method of claim 1, wherein updating a display comprises displaying a message based on the PCR cycle corresponding to a point within a growth period of the amplification data.

8. The method of claim 5, wherein updating a display comprises displaying the $T_{max}$ value.

9. The method of claim 5, wherein the nucleic acid sample comprises a known initial nucleic acid concentration.

10. The method of claim 9, wherein updating a display comprises displaying the $T_{max}$ value on a plot comprising the $T_{max}$ value versus a logarithm of the initial nucleic acid concentration.

11. The method of claim 10, further comprising:
repeating the method of claim 1 for each of a plurality of nucleic acid samples each comprising a known initial nucleic acid concentration.

12. The method of claim 11, wherein the plot further comprises a standard curve fit to the $T_{max}$ values versus logarithm of the initial nucleic acid concentration for each of the plurality of samples using linear regression.

13. The method of claim 12, further comprising:
repeating the method of claim 1 for a nucleic acid sample comprising an unknown initial nucleic acid concentration.

14. The method of claim 13, wherein updating a display comprises displaying a $T_{max}$ value of the nucleic acid sample comprising an unknown initial nucleic acid concentration on the plot.

15. The method of claim 14, further comprising:
determining the initial amount of nucleic acid in the nucleic acid sample comprising an unknown initial nucleic acid concentration based on the $T_{max}$ value of the nucleic acid sample comprising an unknown initial nucleic acid concentration and the standard curve.

16. The method of claim 5, wherein the nucleic acid sample comprises an unknown initial nucleic acid concentration.

17. The method of claim 16, further comprising:
determining an initial concentration of the nucleic acid sample based on the $T_{max}$ value and a standard curve.

18. The method of claim 5, wherein applying wavelet transformation to the amplification data comprises generating a plurality of frequency slices, wherein each of the plurality of frequency slices comprises a plurality of time translation values and wherein each time translation value comprises a wavelet transformation magnitude.

19. The method of claim 18, wherein applying wavelet transformation to the amplification data comprises determining the $T_{max}$ value based on the wavelet transformation magnitude of at least one of the plurality of time translation values.

20. The method of claim 1, wherein applying wavelet transformation to the amplification data comprises applying a Haar wavelet in wavelet transformation to the amplification data.

21. The method of claim 1, wherein applying wavelet transformation to the amplification data comprises selecting a wavelet.

22. The method of claim 18, wherein applying wavelet transformation to the amplification data comprises selecting one of the plurality of frequency slices and determining the $T_{max}$ value based on the wavelet transformation magnitude of at least one of the plurality of time translation values in the frequency slice.

23. A computer-readable medium comprising instructions that cause a processor to:
initiate a PCR analysis of a nucleic acid sample, wherein the PCR analysis comprises a plurality of PCR cycles;
from the PCR analysis, receive amplification data proportional to an amount of nucleic acid present for each of the plurality of PCR cycles;
apply wavelet transformation to the amplification data to determine a PCR cycle corresponding to a point within a growth period of the amplification data; and
update a display based on the PCR cycle corresponding to a point within a growth period of the amplification data.

24. The computer-readable medium of claim 23, wherein the nucleic acid sample comprises an unknown initial amount of nucleic acid, and wherein the computer-readable medium further comprises instructions to cause a processor to:
   determine an initial concentration of the nucleic acid sample based on the PCR cycle corresponding to a point within a growth period of the amplification data and a standard curve.

25. A device comprising:
   a control module that initializes a PCR analysis of a nucleic acid sample and receives amplification data proportional to an amount of nucleic acid present for each of a plurality of PCR cycles;
   an analysis module that applies wavelet transformation to the amplification data and identifies components having the largest local wavelet magnitudes of the transformed amplification data to determine a PCR cycle corresponding to a point within a growth period of the amplification data; and
   an interface module that updates a display based on the PCR cycle corresponding to a point within a growth period of the amplification data.

26. The device of claim 25, wherein the analysis module:
   generates an amplification curve from the amplification data, the amplification curve representing growth of the nucleic acid sample versus PCR cycle; and
   applies continuous wavelet transformation (CWT) to the amplification curve to decompose the amplification curve into frequency components while maintaining PCR cycle localization for the frequency components along the amplification curve.

27. The device of claim 25,
   wherein the amplification data represents growth of the nucleic acid sample over time, and
   wherein the analysis module applies discrete wavelet transformation (DWT) to the amplification data to decompose the amplification data into frequency components while maintaining PCR cycle localization for the frequency components with respect to time.

28. The device of claim 25, wherein the PCR cycle corresponding to a point within a growth period of the amplification data comprises a fraction of a cycle.

29. The device of claim 25, wherein the PCR cycle corresponding to a point within a growth period of the amplification data is referred to as a $T_{max}$ value.

30. The device of claim 25, wherein the PCR cycle corresponding to a point within a growth period of the amplification data corresponds to an approximate onset of the growth period.

31. The device of claim 25, wherein the interface module displays a message based on the PCR cycle corresponding to a point within a growth period of the amplification data.

32. The device of claim 29, wherein the interface module displays the $T_{max}$ value.

33. The device of claim 25, further comprising a database module to store the amplification data.

34. The device of claim 29, wherein the nucleic acid sample comprises a known initial amount of nucleic acid.

35. The device of claim 34, wherein the interface module displays the $T_{max}$ value on a plot comprising the $T_{max}$ versus a logarithm of the initial amount of nucleic acid.

36. The device of claim 35, wherein the analysis module determines a $T_{max}$ value for each of a plurality of nucleic acid samples comprising a known initial amount of nucleic acid.

37. The device of claim 36, wherein the plot further comprises a line fit to the $T_{max}$ value versus logarithm of the initial amount of nucleic acid for each of the plurality of samples using linear regression.

38. The device of claim 37, wherein the analysis module determines a $T_{max}$ value for a nucleic acid sample comprising an unknown initial amount of nucleic acid.

39. The device of claim 38, wherein the interface module displays the $T_{max}$ value of the nucleic acid sample comprising an unknown initial amount of nucleic acid on the plot.

40. The device of claim 39, wherein the analysis module determines the initial amount of nucleic acid in the nucleic acid sample comprising an unknown initial amount of nucleic acid based on the $T_{max}$ value of the nucleic acid sample comprising an unknown initial amount of nucleic acid and the line.

41. The device of claim 29, wherein the nucleic acid sample comprises an unknown initial amount of nucleic acid.

42. The device of claim 41, wherein the analysis module determines an initial concentration of the nucleic acid sample based on the $T_{max}$ value and a standard curve.

43. The device of claim 29, wherein the analysis module applies wavelet transformation to the amplification data to generate a plurality of frequency slices, wherein each of the plurality of frequency slices comprises a plurality of time translation values and wherein each time translation value comprises a wavelet amplitude.

44. The device of claim 43, wherein the analysis module determines a $T_{max}$ value based on the wavelet amplitude of at least one of the plurality of time translation values.

45. The device of claim 25, wherein the analysis module applies a Haar wavelet to the amplification data.

46. The device of claim 25, wherein applying wavelet transformation to the amplification data comprises selecting a wavelet.

47. The device of claim 43, wherein the analysis module selects one of the plurality of frequency slices and determines a $T_{max}$ value based on the wavelet transformation magnitude of at least one of the plurality of time translation values in the frequency slice.

* * * * *